(12) United States Patent
Androsov et al.

(10) Patent No.: US 12,037,304 B2
(45) Date of Patent: Jul. 16, 2024

(54) MONOMER AND POLYMER, COMPENSATION FILM, OPTICAL FILM, AND DISPLAY DEVICE

(71) Applicant: SAMSUNG ELECTRONICS CO., LTD., Suwon-si (KR)

(72) Inventors: Dmitry Androsov, Suwon-si (KR); Hyunseok Choi, Seoul (KR); Kalinina Fedosya, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 18/062,340

(22) Filed: Dec. 6, 2022

(65) Prior Publication Data

US 2023/0192592 A1 Jun. 22, 2023

Related U.S. Application Data

(62) Division of application No. 16/053,085, filed on Aug. 2, 2018, now Pat. No. 11,518,734.

(30) Foreign Application Priority Data

Aug. 2, 2017 (KR) .................. 10-2017-0098286
Aug. 1, 2018 (KR) .................. 10-2018-0089691

(51) Int. Cl.
| | | |
|---|---|---|
| C08G 73/00 | (2006.01) | |
| C07C 219/34 | (2006.01) | |
| C07C 229/60 | (2006.01) | |
| C07C 235/42 | (2006.01) | |
| C07D 277/64 | (2006.01) | |
| C08G 73/10 | (2006.01) | |
| C08G 73/14 | (2006.01) | |
| C08G 73/16 | (2006.01) | |
| C09D 179/08 | (2006.01) | |
| G02B 1/04 | (2006.01) | |
| G02B 5/30 | (2006.01) | |

(52) U.S. Cl.
CPC .......... *C07C 219/34* (2013.01); *C07C 229/60* (2013.01); *C07C 235/42* (2013.01); *C07D 277/64* (2013.01); *C08G 73/1007* (2013.01); *C08G 73/1039* (2013.01); *C08G 73/1042* (2013.01); *C08G 73/1067* (2013.01); *C08G 73/14* (2013.01); *C08G 73/16* (2013.01); *C09D 179/08* (2013.01); *G02B 1/04* (2013.01); *G02B 5/3083* (2013.01); *G02B 5/3025* (2013.01)

(58) Field of Classification Search
CPC ...... C08G 73/16; C08G 73/00; C07C 219/32; C07C 229/60
See application file for complete search history.

(56) References Cited

U.S. PATENT DOCUMENTS

| | | |
|---|---|---|
| 3,541,054 A | 11/1970 | Tohru et al. |
| 5,202,410 A | 4/1993 | Irwin |
| 9,200,117 B2 | 12/2015 | Cho et al. |
| 9,796,816 B2 | 10/2017 | Cho et al. |
| 2016/0039977 A1 | 2/2016 | Cho et al. |
| 2017/0006282 A1 | 3/2017 | Hwang et al. |
| 2017/0062826 A1 | 3/2017 | Hwang et al. |

FOREIGN PATENT DOCUMENTS

| | | |
|---|---|---|
| CN | 106486675 A | 3/2017 |
| JP | 45033670 | 3/1967 |
| JP | 20063715 A | 1/2006 |
| JP | 2008255037 A | 10/2008 |
| JP | 2011141448 A | 7/2011 |
| JP | 2012241196 A | 12/2012 |
| JP | 2013069466 A | 4/2013 |
| JP | 2018145771 A | 9/2018 |
| KR | 1020130029129 A | 3/2013 |
| WO | 2018159733 A1 | 9/2018 |

OTHER PUBLICATIONS

Andreea Irina Barzic, et al., "Semi-Alicyclic Polyimides: Insights into Optical Properties and Morphology Patterning Approaches for Advanced Technologies", High Performance Polymers—Polymides Based—From Chemistry to Applications, 32 pp.
English Abstract of JP 2018-145771.
English Translation of Notice of Allowance dated Jul. 2, 2020 of the corresponding Korean Patent Application No. 10-2018-008969.
English Translation of Office Action dated Jul. 12, 2022, of the corresponding Chinese Patent Application No. 201810869335.5, 16 pp.

(Continued)

*Primary Examiner* — Gregory Listvoyb
(74) *Attorney, Agent, or Firm* — CANTOR COLBURN LLP

(57) ABSTRACT

A monomer represented by Chemical Formula 1:

Chemical Formula 1

$(R^1)_o$—$A^1$—$(CH_2)_p$—$L^1$—[structure with NH$_2$ groups]—$L^2$—$(CH_2)_q$—$A^2$—$(R^2)_r$ wherein, in Chemical Formula 1, $R^1$, $R^2$, $A^1$, $A^2$, $L^1$, $L^2$, o, p, q, and r are the same as defined in the detailed description.

19 Claims, 9 Drawing Sheets

(56) References Cited

OTHER PUBLICATIONS

English Translation of Office Action dated Jun. 27, 2022, of the corresponding Japanese Patent Application No. 2018-145771, 7 pp.
Extended European Search Report dated Jan. 8, 2019, of the corresponding European Patent Application No. 18186656.7.
Masatoshi Hasegawa, et al., "Optically transparent aromatic poly-(ester imide)s with low coefficients of thermal expansion (1). Self-orientation behavior during solution casting process and substituent effect", Polymer 74 (2015) 1-15.
Notice of Allowance dated Jul. 2, 2020 of the corresponding Korean Patent Application No. 10-2018-008969.
Office Action dated Jul. 12, 2022, of the corresponding Chinese Patent Application No. 201810869335.5, 11 pp.

MONOMER AND POLYMER, COMPENSATION FILM, OPTICAL FILM, AND DISPLAY DEVICE

CROSS-REFERENCE TO RELATED APPLICATION

This application is a divisional application of U.S. patent application Ser. No. 16/053,085 filed on Aug. 2, 2018, now U.S. Pat. No. 11,518,734, which in turn claims priority to Korean Patent Application No. 10-2017-0098286 filed in the Korean Intellectual Property Office on Aug. 2, 2017 and Korean Patent Application No. 10-2018-0089691 filed in the Korean Intellectual Property Office on Aug. 1, 2018, and all the benefits accruing therefrom under 35 U.S.C. § 119, 120, the contents of which here in their entirety are herein incorporated by reference.

BACKGROUND

1. Field

A monomer, a polymer, a compensation film, an optical film, and a display device are disclosed.

2. Description of the Related Art

Research efforts have been undertaken to produce a colorless transparent material that is suitable for diverse purposes such as for an optical lens, a functional optical film, and a disk substrate. However, as information devices are being further miniaturized and display devices are providing higher resolution, more functions and greater performance are required from the material.

Therefore, research efforts are currently underway to develop a colorless transparent material having improved transparency, heat resistance, mechanical strength, and flexibility.

SUMMARY

An embodiment provides a novel monomer that is applicable to a compensation film.

Another embodiment provides a polymer obtained by polymerizing the novel monomer.

Yet another embodiment provides a compensation film including the polymer.

Still another embodiment provides an optical film including the compensation film.

Further embodiment provides a display device including the compensation film or the optical film.

An embodiment provides a monomer represented by Chemical Formula 1:

Chemical Formula 1

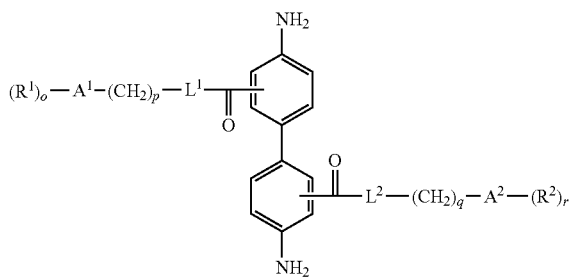

wherein, in Chemical Formula 1,
$L^1$ and $L^2$ are independently O or $NR^b$ (wherein, $R^b$ is hydrogen or a C1 to C20 alkyl group),
$A^1$ and $A^2$ are independently a C6 to C30 aromatic ring or a C3 to C30 hetero aromatic ring,
p and q are independently an integer ranging from 0 to 20, and r are independently an integer ranging from 0 to 3, and
$R^1$ and $R^2$ are independently hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C2 to C30 heteroaryl group, a substituted or unsubstituted C7 to C30 arylalkyl group, a hydroxy group, a halogen, a nitro group, —NR'R", —CO—NR'R", —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

Chemical Formula 2

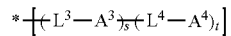

wherein, in Chemical Formula 2,
$L^3$ and $L^4$ are independently O, CO, COO, C≡C, or $CONR^b$ (wherein, $R^b$ is hydrogen or a C1 to C30 alkyl group),
$A^3$ and $A^4$ are independently a substituted or unsubstituted C6 to C30 aromatic ring group, a substituted or unsubstituted fluorene ring, a substituted or unsubstituted C7 to C30 arylalkyl group, or a substituted or unsubstituted C3 to C30 hetero aromatic ring group, and
s and t are independently an integer ranging from 0 to 3.
In Chemical Formula 1,
$L^1$ and $L^2$ may independently be O or NH,
$A^1$ and $A^2$ may independently be a C6 to C20 aromatic ring or a C3 to C20 hetero aromatic ring wherein at least one carbon is replaced by at least one of nitrogen and sulfur,
p and q may independently be an integer ranging from 1 to 6,
and r may independently be an integer ranging from 0 to 2, and
$R^1$ and $R^2$ may independently be hydrogen, a C1 to C20 alkyl group, a C1 to C10 alkoxy group, a C6 to C20 aryl group, a C2 to C20 heteroaryl group, a C7 to C20 arylalkyl group, a halogen, a nitro group, —CO—NR'R" (wherein, R' and R" are independently hydrogen, a C1 to C30 alkyl group, a C6 to C30 aryl group, or a C7 to C30 arylalkyl group), or a group represented by Chemical Formula 2:

Chemical Formula 2

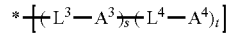

wherein, in Chemical Formula 2,
$L^3$ and $L^4$ may independently be O, CO, COO, C≡C, or CONN,
$A^3$ and $A^4$ may independently be a substituted or unsubstituted C6 to C20 aromatic ring group, or a substituted or unsubstituted C3 to C20 heteroaromatic ring group wherein at least one carbon is replaced by at least one of nitrogen and sulfur, and s and t may independently be an integer ranging from 0 to 2, provided that 1≤s+t≤2.

In Chemical Formula 1, $L^1$ and $L^2$ may independently be O or NH, $A^1$ and $A^2$ may independently be selected from benzene, naphthalene, anthracene, pentalene, pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine, p and q may independently be 1 or 2, and r may independently be 0 or 1, and $R^1$ and $R^2$ may independently be hydrogen, a C1 to C10 alkyl group, a C1 to 010 alkoxy group, a C6 to C10 aryl group, a halogen, a nitro group, —CO—NR'R" (wherein, R' and R" are independently hydrogen, a C1 to C20 alkyl group, a C6 to C20 aryl group, or a C7 to C20 arylalkyl group), or a group represented by Chemical Formula 2:

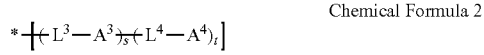

Chemical Formula 2 wherein, in Chemical Formula 2, $L^3$ and $L^4$ may independently be COO, C≡C, or CONN, $A^3$ and $A^4$ may be a substituted or unsubstituted benzene ring, and s and t may independently be an integer ranging from 0 to 2, provided that 1≤s+t≤2.

The monomer represented by Chemical Formula 1 may be represented by Chemical Formula 3:

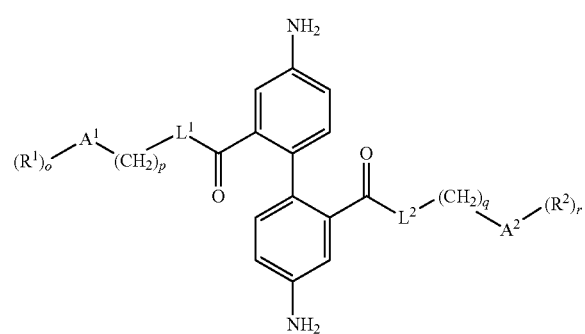

Chemical Formula 3 wherein, in Chemical Formula 3, $L^1$, $L^2$, $A^1$, $A^2$, $R^1$, $R^2$, o, p, q, and r are the same as defined in Chemical Formula 1.

In Chemical Formula 3, $L^1$ and $L^2$ may independently be O or NH, $A^1$ and $A^2$ may independently be a C6 to C20 aromatic ring or a C3 to C20 hetero aromatic ring wherein at least one carbon is replaced by at least one of nitrogen and sulfur, p and q may independently be an integer ranging from 1 to 6, and r may independently be an integer ranging from 0 to 2, and $R^1$ and $R^2$ may independently be hydrogen, a C1 to C20 alkyl group, a C1 to C10 alkoxy group, a C6 to C20 aryl group, a C2 to C20 heteroaryl group, a C7 to C20 arylalkyl group, a nitro group, a halogen, —CO—NR'R" (wherein, R' and R" are independently hydrogen, a C1 to C30 alkyl group, a C6 to C30 aryl group, or a C7 to C30 arylalkyl group), or a group represented by Chemical Formula 2:

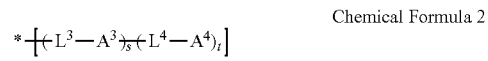

Chemical Formula 2 wherein, in Chemical Formula 2, $L^3$ and $L^4$ may independently be O, CO, COO, C≡C, or CONH, $A^3$ and $A^4$ may independently be a substituted or unsubstituted C6 to C20 aromatic ring group or a substituted or unsubstituted C3 to C20 heteroaromatic ring group wherein at least one carbon is replaced by at least one of nitrogen and sulfur, and s and t may independently be an integer ranging from 0 to 2, provided that 1≤s+t≤2.

In Chemical Formula 3, $L^1$ and $L^2$ may independently be O or NH, $A^1$ and $A^2$ may independently be selected from benzene, naphthalene, anthracene, pentalene, pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine, p and q may independently be 1 or 2, and r may independently be 0 or 1, and $R^1$ and $R^2$ may independently be hydrogen, a C1 to C10 alkyl group, a C1 to C10 alkoxy group, a C6 to C10 aryl group, a halogen, a nitro group, —CO—NR'R" (wherein, R' and R" are independently hydrogen, a C1 to C20 alkyl group, a C6 to C20 aryl group, or a C7 to C20 arylalkyl group), or a group represented by Chemical Formula 2:

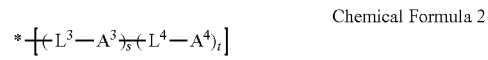

Chemical Formula 2 wherein, in Chemical Formula 2, $L^3$ and $L^4$ may independently be COO, C≡C, or CONH, $A^3$ and $A^4$ may be a substituted or unsubstituted benzene ring, and s and t may independently be an integer ranging from 0 to 2, provided that 1≤s+t≤2.

In Chemical Formula 3, $L^1$ and $L^2$ may independently be O or NH, $A^1$ and $A^2$ may independently be selected from benzene, naphthalene, or benzothiazole, p and q may independently be 1 or 2, and r may independently be 0 or 1, and $R^1$ and $R^2$ may independently be hydrogen, an iso-propyl group, a t-butyl group, a fluorine group, a nitro group, a methoxy group, an ethoxy group, —CO—NR'R" (wherein, R' and R" are independently hydrogen, a C1 to C10 alkyl group, or a C6 to C10 aryl group), or a group represented by Chemical Formula 2:

Chemical Formula 2

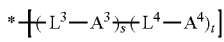

wherein in Chemical Formula 2, $L^3$ and $L^4$ may independently be COO, C≡C, or CONN, $A^3$ and $A^4$ may independently be a substituted or unsubstituted benzene ring, and s and t may independently be an integer ranging from 0 to 2, provided that 1≤s+t≤2.

In another embodiment, a polymer is a reaction product of reactants including the monomer according to the embodiment and dianhydride.

The dianhydride may be represented by Chemical Formula 4-1 or Chemical Formula 4-2:

Chemical Formula 4-1

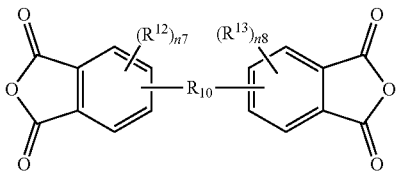

wherein in Chemical Formula 4-1, $R^{10}$ is a single bond, —O—, —S—, —C(=O)—, —CH(OH)—, —C(=O)NH—, —S(=O)$_2$—, —Si(CH$_3$)$_2$—, —(CH$_2$)$_p$—, —(CF$_2$)$_q$—, —C(C$_n$H$_{2n+1}$)$_2$—, —C(C$_n$F$_{2n+1}$)$_2$—, —(CH$_2$)$_p$—C(C$_n$H$_{2n+1}$)$_2$—(CH$_2$)$_q$—, or —(CH$_2$)$_p$—C(C$_n$F$_{2n+1}$)$_2$—(CH$_2$)$_q$— (wherein 1≤n≤10, 1≤p≤10, and 1≤q≤10), $R^{12}$ and $R^{13}$ are independently a halogen, a hydroxy group, a substituted or unsubstituted C1 to C10 aliphatic organic group, a substituted or unsubstituted C6 to C20 aromatic organic group, a —OR$^{201}$ group (wherein R$^{201}$ is a C1 to C10 aliphatic organic group), or a —SiR$^{210}$R$^{211}$R$^{212}$ (wherein R$^{210}$, R$^{211}$, and R$^{212}$ are independently hydrogen or a C1 to C10 aliphatic organic group) group, and n7 and n8 are independently one of integers of 0 to 3.

Chemical Formula 4-2

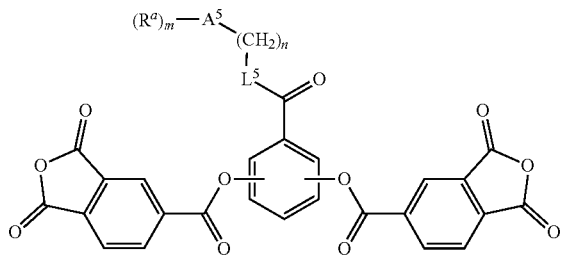

wherein, in Chemical Formula 4-2, $L^5$ is O or NR$^b$ (wherein, R$^b$ is hydrogen or a C1 to C20 alkyl group), $A^5$ is a C6 to C30 aromatic organic group, $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R", —CO—NR'R", —SiR'R"R'" (wherein R', R", and R'" are independently hydrogen, a C1 to C30 alkyl group, a C6 to C30 aryl group, or a C7 to C30 arylalkyl group), or a group represented by Chemical Formula A:

Chemical Formula A

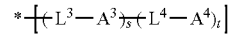

wherein, in Chemical Formula A, $L^3$ and $L^4$ are independently O, CO, COO, C≡C, or CONR$^b$ (wherein, R$^b$ is hydrogen or a C1 to C30 alkyl group), $A^3$ and $A^4$ are independently a substituted or unsubstituted C6 to C30 aromatic ring, a substituted or unsubstituted fluorene ring, or a substituted or unsubstituted C7 to C30 arylalkyl group, s and t are independently an integer ranging from 0 to 3, m of Chemical Formula 4-2 is an integer ranging from 0 to 3, and n is an integer ranging from 0 to 20.

The dianhydride represented by Chemical Formula 4-1 may include dianhydride represented by Chemical Formula 5-1, dianhydride represented by Chemical Formula 6-1, or a combination thereof and the dianhydride represented by Chemical Formula 4-2 may include dianhydride represented by Chemical Formula 5-2, dianhydride represented by Chemical Formula 6-2, or a combination thereof:

Chemica Formula 5-1

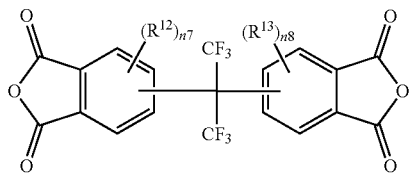

Chemical Formula 6-1

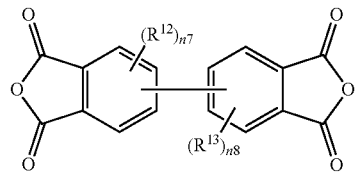

wherein, in Chemical Formula 5-1 and Chemical Formula 6-1, $R^{12}$ and $R^{13}$ are the same or different and are independently a halogen, a hydroxy group, an alkoxy group (—OR$^{2138}$, wherein R$^{208}$ is a C1 to C10 aliphatic organic group), a silyl group (—SiR$^{209}$R$^{210}$R$^{211}$, wherein R$^{209}$, R$^{210}$, and R$^{211}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n7 and n8 are independently an integer ranging from 0 to 3;

Chemical Formula 5-2

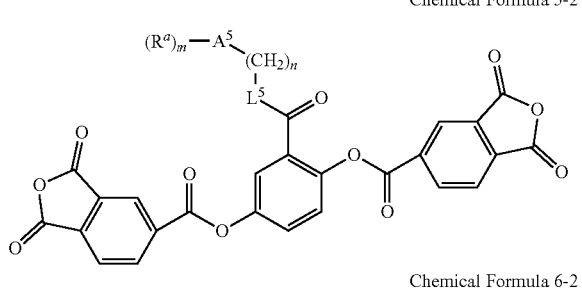

Chemical Formula 6-2

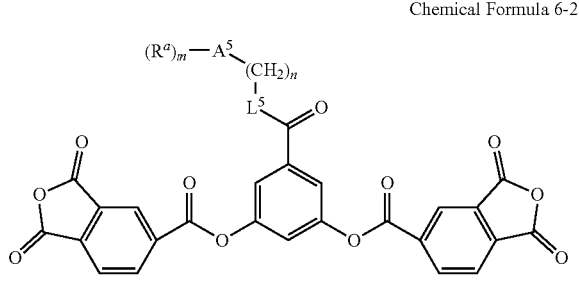

wherein, in Chemical Formula 5-2 and Chemical Formula 6-2, $L^5$, $A^5$, $R^a$, m, and n are the same as defined in Chemical Formula 4-2.

The polymer may be a product of reactants further including a dicarboxylic acid derivative represented by Chemical Formula 7:

Chemical Formula 7

wherein, in Chemical Formula 7,
$R^3$ is at least one of a substituted or unsubstituted phenylene group and a substituted or unsubstituted biphenylene group, and each of X is the same or different and is a halogen atom.

In Chemical Formula 7,
$R^3$ may be at least one of an unsubstituted phenylene group and an unsubstituted biphenylene group, and X may independently be Cl or Br.

The polymer may be a product of reactants further including diamine represented by Chemical Formula 8:

$NH_2—R^c—NH_2$      Chemical Formula 8

wherein, in Chemical Formula 8,
$R^c$ is a substituted or unsubstituted C6 to C30 aromatic organic group, wherein the substituted or unsubstituted C6 to C30 aromatic organic group is present as a substituted or unsubstituted single aromatic ring; a fused ring including two or more substituted or unsubstituted aromatic rings; or a ring system including two or more of the substituted or unsubstituted single aromatic ring and/or the fused ring that are linked by a single bond, or a functional group selected from a fluorenylene group, a substituted or unsubstituted C1 to C10 cycloalkylene group, a substituted or unsubstituted C6 to C15 arylene group, —O—, to —S—, —C(=O)—, —CH(OH)—, —S(=O)$_2$—, —Si(CH$_3$)$_2$—, —(CH$_2$)$_p$— (wherein, 1≤p≤10), —(CF$_2$)$_q$— (wherein, 1≤q≤10), —C(CH$_3$)$_2$—, —C(CF$_3$)$_2$—, —C(=O)NH—, or a combination thereof.

The diamine represented by Chemical Formula 8 may be represented by at least one of Chemical Formula 9 to Chemical Formula 11:

Chemical Formula 9

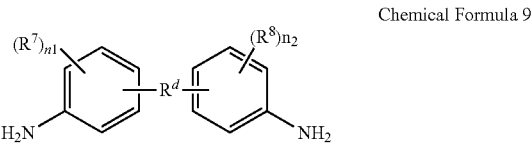

wherein, in Chemical Formula 9,
$R^d$ is selected from the following chemical formulae:

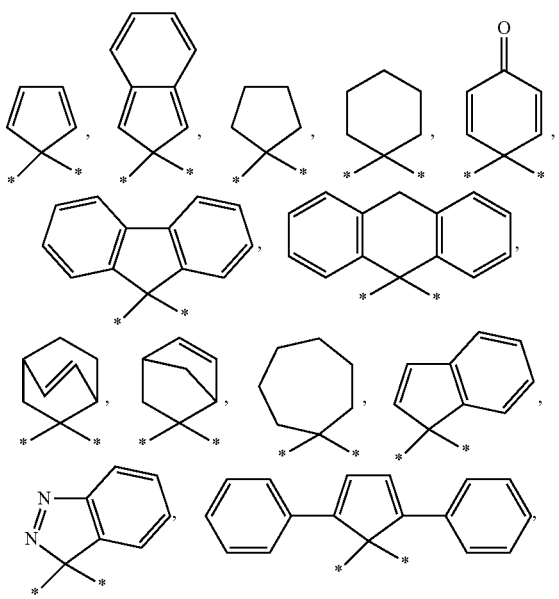

$R^7$ and $R^8$ are the same or different and are independently a halogen, a hydroxy group, an alkoxy group (—OR$^{200}$, wherein $R^{206}$ is a C1 to C10 aliphatic organic group), a silyl group (—SiR$^{201}$R$^{202}$R$^{203}$, wherein $R^{201}$, $R^{202}$, and $R^{203}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and
n1 and n2 are independently an integer ranging from 0 to 4;

Chemical Formula 10

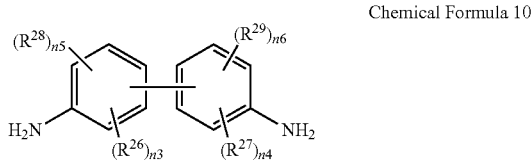

wherein, in Chemical Formula 10,
$R^{26}$ and $R^{27}$ are the same or different and are independently an electron withdrawing group selected from —CF$_3$, —CCl$_3$, —CBr$_3$, —Cl$_3$, —NO$_2$, —CN, —COCH$_3$, or —CO$_2$O$_2$H$_5$,
$R^{28}$ and $R^{29}$ are the same or different and are independently a halogen, a hydroxy group, an alkoxy group (—OR$^{204}$, wherein R$^{204}$ is a C1 to C10 aliphatic organic group), a silyl group (—SiR$^{205}$R$^{206}$R$^{207}$, wherein R$^{206}$, R$^{206}$, and R$^{207}$ are the same or different and are independently hydrogen or a C1 to C10 aliphatic organic group), a substituted or unsubstituted C1 to C10 aliphatic organic group, or a substituted or unsubstituted C6 to C20 aromatic organic group, n3 is an integer ranging from 1 to 4, and n5 is an integer ranging from 0 to 3, provided that n3+n5 is an integer ranging from 1 to 4, and n4 is an integer ranging from 1 to 4, and n6 is an integer ranging from 0 to 3, provided that n4+n6 is an integer ranging from 1 to 4;

Chemical Formula 11

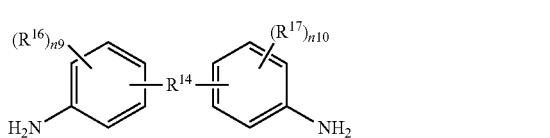

wherein, in Chemical Formula 11,

R$^{14}$ includes O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, C(=O)NH, or a substituted or unsubstituted C6 to C18 aromatic organic group, wherein the substituted or unsubstituted C6 to C18 aromatic organic group is present as a single aromatic ring, a fused ring including two or more aromatic rings, or a ring system including two or more of the single aromatic ring and/or the fused ring that are linked by a single bond or a functional group selected from a fluorenylene group, O, S, C(=O), CH(OH), S(=O)$_2$, Si(CH$_3$)$_2$, (CH$_2$)$_p$ (wherein, 1≤q≤10), (CF$_2$)$_q$ (wherein, 1≤q≤10), C(CH$_3$)$_2$, C(CF$_3$)$_2$, or C(=O)NH, R$^{16}$ and R$^{17}$ are the same or different and are independently a halogen, a hydroxy group, an alkoxy group (—OR$^{212}$, wherein R$^{212}$ is a C1 to C10 aliphatic organic group), a silyl group (—SiR$^{213}$R$^{214}$R$^{215}$, wherein R$^{213}$, R$^{214}$, and R$^{215}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n9 and n10 are independently an integer ranging from 0 to 4.

The diamine represented by Chemical Formula 8 may include at least one of the diamine represented by Chemical Formula 10 and the diamine represented by Chemical Formula 11, the diamine represented by Chemical Formula 10 may include 2,2'-bis(trifluoromethyl)benzidine (TFDB), and the diamine represented by Chemical Formula 11 may include 4,4'-diaminodiphenyl sulfone (DADPS).

An amount of the diamine represented by Chemical Formula 8 may be less than or equal to about 50 mole percent based on a total amount of the monomer represented by Chemical Formula 1 and the diamine represented by Chemical Formula 8.

Another embodiment provides a compensation film including the polymer according to the embodiment.

Another embodiment provides an optical film including the compensation film according to the embodiment and a polarizer.

Another embodiment provides a display device including the compensation film according to the embodiment.

Another embodiment provides a display device including the optical film according to the embodiment.

Hereinafter, the embodiments are described in detail.

A novel monomer, according to an embodiment, reacts with dianhydride, and thus, may be used to form a polyimide film having high transmittance, a low yellow index, and low haze, as well as a high out-of-plane birefringence. The novel monomer is prepared from inexpensive raw materials, and accordingly, may be used to manufacture an optical film requiring high optical characteristics and mechanical properties.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
FIG. 1 is a schematic cross-sectional view of an optical film, according to an embodiment.

Hereinafter, exemplary embodiments will be described in detail, and may be readily performed by those who have common knowledge in the related art. However, this disclosure may be embodied in many different forms and should not be construed as limited to the exemplary embodiments set forth herein.

Accordingly, the embodiments are merely described below, by referring to the figures, to explain aspects of the present description. As used herein, the term "and/or" includes any and all combinations of one or more of the associated listed items. The term "or" means "and/or." Expressions such as "at least one of" when preceding a list of elements, modify the entire list of elements and do not modify the individual elements of the list.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or non-linear features. Moreover, sharp angles that are illustrated may be rounded. Thus, the regions illustrated in the figures are schematic in nature and their shapes are not intended to illustrate the precise shape of a region and are not intended to limit the scope of the present claims.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, the term "substituted" refers to replacement of a hydrogen atom of a compound or a functional group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, the term "hetero" refers to inclusion of 1 to 3 hetero atoms selected from N, O, S, Se, and P.

As used herein, when a definition is not otherwise provided, the term "alkyl" indicates a group derived from a completely saturated, branched or unbranched (or a straight or linear) hydrocarbon and having a specified number of carbon atoms.

As used herein, the term "cycloalkyl group" refers to a monovalent group having one or more saturated rings in which all ring members are carbon. Non-limiting examples of the cycloalkyl group are cyclopentyl and cyclohexyl.

As used herein, when a definition is not otherwise provided, the term "alkoxy" represents "alkyl-O—", wherein the term "alkyl" has the same meaning as described above.

As used herein, when a definition is not otherwise provided, the term "cycloalkoxy" represents "cycloalkyl-O—", wherein the term "cycloalkyl" has the same meaning as described above.

As used herein, when a definition is not otherwise provided, the term "aryl" indicates an aromatic hydrocarbon containing at least one ring and having the specified number of carbon atoms.

As used herein, when a definition is not otherwise provided, the term "arylalkyl" represents "aryl-alkyl-", wherein the terms "aryl" and "alkyl" have the same meaning as described above.

As used herein, the term "alkylene" indicates a group having one or more saturated rings in which all ring members are carbon having a valence of at least two, optionally substituted with one or more substituents where indicated, provided that the valence of the cycloalkylene group is not exceeded.

As used herein, the term "cycloalkylene" indicates a straight or branched saturated aliphatic hydrocarbon group having a valence of at least two, optionally substituted with one or more substituents where indicated, provided that the valence of the alkylene group is not exceeded.

As used herein, when a definition is not otherwise provided, the term "arylene" indicates a divalent group formed by the removal of two hydrogen atoms from one or more rings of an arene, wherein the hydrogen atoms may be removed from the same or different rings of the arene.

An optically transparent heat resistant polymer described herein may be applied to various optoelectronic devices, for example, an image device, a liquid crystal alignment layer, a color filter, an optical compensation film, an optic fiber, a light guide, optical lens, and the like. In this regard, research efforts have been recently made to realize a remarkably light and flexible display panel by replacing a fragile inorganic glass substrate (e.g., about 300 nanometers (nm) to about 700 millimeters (mm) thick) in an image device with a plastic substrate (<about 50 mm thick) has drawn attention.

However, the plastic substrate has not secured reliability yet, because it is difficult to simultaneously achieve optical transmittance, heat resistance, dimensional stability (thermal dimensional stability) at a thermal cycle during the assembly process of a device, film flexibility, and film-forming process compatibility (a solution process) in a high level. The plastic substrate is excellent in terms of flexibility and thin film formality, but inferior in terms of heat resistance and thermal dimensional stability compared with the inorganic glass substrate.

Poly(ether sulfone) (PES) is known to have the highest glass transition temperature ($T_g$, 225° C.) among commercially available super engineering plastics. However, PES may be unsuitable for the plastic substrate in terms of heat resistance and thermal dimensional stability. A plastic substrate having insufficient thermal dimensional stability may be thermally expanded/contracted during repetitive heating/cooling cycles in a process of forming an ITO (indium tin oxide) electrode and a thin film transistor, and thus, may cause a serious problem of destroying an ITO layer.

A high temperature polymer material having the highest reliability may be polyimide (PI). A part of aromatic PI systems simultaneously has much higher T g than a device operating temperature and a low linear coefficient of thermal expansion (CTE) along a film plane (X-Y) direction in a glassy region, and thus, excellent thermal dimensional stability. However, common aromatic PI is strongly colored due to a charge transfer (CT) interaction and often disturbs an optical device. Accordingly, academic and industrial research efforts on a coloring/discoloring mechanism of an aromatic PI film have been widely conducted. One of the effective approaches for discoloring the film is to block the CT interaction by selecting a non-aromatic (alicyclic) monomer from diamine, tetracarboxylic dianhydride, or both of them. However, the alicyclic monomer may cause a serious problem in some uses. In other words, a partly or wholly alicyclic PI film often has insufficient thermal dimensional stability due to a high linear coefficient of thermal expansion CTE (>60 parts per million per Kelvin (ppm $K^{-1}$)) in the glassy region despite a high glass transition temperature $T_g$ (>300° C.). This high linear coefficient of thermal expansion is actually generated from a randomly three dimensionally disposed chain alignment. The alicyclic monomer mostly has a non-linear/non-planar cubic structure. As a result, linearity of a PI main chain is completely destroyed. In this twisted backbone structure, chains may not be highly aligned along an X-Y direction (hereinafter, "planar alignment") during a thermal imidization process. Among the alicyclic monomers, 1,2,3,4-cyclobutane tetracarboxylic dianhydride (CBDA) and trans-1,4-cyclohexane diamine (t-CHDA) uncommonly has a rigid and linear structure. However, a final PI using this monomer may not be applied to a solution process. However, a wholly aromatic PI system induced from 4,4'-(hexafluoroisopropylidene) diphthalic anhydride (6FDA) and 2,2'-bis(trifluoromethyl)benzidine (TFMB) has no low coefficient of thermal expansion due to a non-linear/non-coplanar cubic structure of a 6-FDA-based diimide unit but high transparency and excellent solubility.

Accordingly, a plastic material simultaneously satisfying desired various characteristics, and thus, having high reliability is difficult to develop.

The present inventors synthesize a novel monomer capable of forming polyimide simultaneously satisfying thermal stability and optical transparency, and thus, has completed the present inventive concept by confirming that a polymer formed from the monomer has a thermal stability due to a high glass transition temperature, as well as particular optical properties, for example, high out-of-plane birefringence along with high transparency. The monomer may be represented by Chemical Formula 1:

Chemical Formula 1

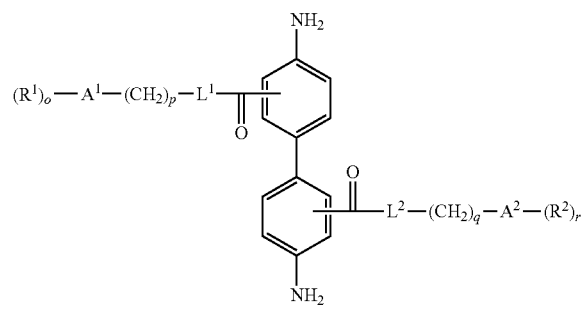

wherein, in Chemical Formula 1,
$L^1$ and $L^2$ are independently O or $NR^b$ (wherein, $R^b$ is hydrogen or a C1 to C20 alkyl group),
$A^1$ and $A^2$ are independently a C6 to C30 aromatic ring or a C3 to C30 hetero aromatic ring,
p and q are independently an integer ranging from 0 to 20, and r are independently an integer ranging from 0 to 3,
$R^1$ and $R^2$ are independently hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C2 to C30 heteroaryl group, a substituted or unsubstituted C7 to C30 arylalkyl group, a hydroxy group, a halogen, a nitro group, —NR'R", —CO—NR'R", —SiR'R"R'" (wherein R', R", and R'" are independently hydrogen, a C1 to C30 alkyl group, a C6 to C30 aryl group, or a C7 to C30 arylalkyl group), or a group represented by Chemical Formula 2:

Chemical Formula 2

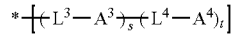

wherein, in Chemical Formula 2,
$L^3$ and $L^4$ are independently O, CO, COO, C≡C, or $CONR^b$ (wherein, $R^b$ is hydrogen or a C1 to C30 alkyl group), $A^3$ and $A^4$ are independently a substituted or unsubstituted C6 to C30 aromatic ring, a substituted or unsubstituted fluorene ring, a substituted or unsubstituted C7 to C30 arylalkyl group, or a substituted or unsubstituted C3 to C30 hetero aromatic ring group, and s and t are independently an integer ranging from 0 to 3.

The compound represented by Chemical Formula 1, according to an embodiment, has an overall rigid planar structure, wherein two aromatic rings are linearly linked and also, includes a bulky substituent at a side chain of the aromatic rings, and thus, may improve solubility due to a much higher molecular volume, and in addition, may improve optical characteristics by suppressing formation of an intermolecular stacking structure of a polyimide or poly (amide-imide) copolymer and decreasing charge transfer when amino groups bound at both ends of two aromatic ring bind dianhydride or dicarboxylic anhydride to form a polyimide or poly(amide-imide) copolymer. The rigid planar structure has a much lower linear coefficient of thermal expansion, a high glass transition temperature, a high out-of-plane birefringence, high mechanical properties, and the like, but may easily form an intermolecular stacking structure, and thus, form an intermolecular charge transfer complex, and accordingly, a polymer formed therefrom appears yellow and deteriorates optical properties. The compound represented by Chemical Formula 1 according to the embodiment has a rigid planar structure overall, but includes a bulky substituent at a side chain of a core, and thus, may suppress formation of a complex among polymer chains and a charge transfer complex therefrom, and thus, reduce a deterioration of optical properties and simultaneously maintain high thermal stability, a low linear coefficient of thermal expansion, a high out-of-plane birefringence, and excellent mechanical properties due to the overall planar structure. Accordingly, polyimide by reacting the monomer, according to an embodiment, with aromatic dianhydride or the poly (amide-imide) copolymer by reacting the monomer, according to an embodiment, with aromatic dianhydride and aromatic dicarboxylic acid derivative may satisfy high thermal stability and excellent optical properties. Furthermore, the compound according to the embodiment may be prepared from easily available inexpensive starting materials, as shown through Examples that will be described later, and thus, may lower a preparation cost compared with a conventional particularly expensive aromatic diamine or an aromatic dianhydride showing excellent optical properties, mechanical properties, and the like.

In an exemplary embodiment, $L^1$ and $L^2$ of Chemical Formula 1 may independently be O or NH, and for example, $L^1$ and $L^2$ may be O, and $A^1$ and $A^2$ may independently be a C6 to C20 aromatic ring or a C3 to C20 hetero aromatic ring wherein at least one carbon is replaced by at least one of nitrogen and sulfur, for example, an arylene group selected from benzene, naphthalene, anthracene, and pentalene or a heteroarylene group selected from pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine.

In an exemplary embodiment, $A^1$ and $A^2$ may independently be an arylene group such as benzene, naphthalene, or anthracene or may independently be a heteroarylene group selected from benzimidazole, benzothiazole, benzothiophene, benzopurine, isoquinoline, or purine.

In an exemplary embodiment, p and q of Chemical Formula 1 may independently be an integer ranging from 1 to 6, for example, p and q may independently be an integer of 1 or 2, for example, p and q may be all 1, o and r may independently be an integer ranging from 0 to 2, for example, o and r may independently be an integer of 1 or 2, for example, o and r may be all 0 or may be all 1.

In an exemplary embodiment, in Chemical Formula 1, $R^1$ and $R^2$ may independently be hydrogen, a C1 to C20 alkyl group, for example, one of a methyl group, an ethyl group, a propyl group, a butyl group, a pentyl group, a hexyl group, a heptyl group, an octyl group, a nonyl group and a decyl group, for example, an iso-propyl group, or a tertiary butyl group (t-butyl group), a C6 to C10 aryl group, for example, a phenyl group or a naphthyl group, a C1 to C10 alkoxy group, for example, a methoxy group, an ethoxy group, or a propoxy group, or a hydroxy group, a halogen, for example, a fluoro group, a nitro group, —CO—NR'R'' (wherein, R' and R'' are independently hydrogen, a C1 to C20 alkyl group, or a C6 to C20 aryl group), or a group represented by Chemical Formula 2:

Chemical Formula 2

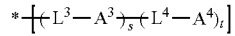

wherein, in Chemical Formula 2, $L^3$ and $L^4$ are independently O, CO, COO, C≡C, or CONK $A^3$ and $A^4$ are independently a substituted or unsubstituted C6 to C20 aromatic ring group, or a substituted or unsubstituted C3 to C20 hetero aromatic ring group wherein at least one carbon is replaced by at least one of nitrogen and sulfur, and s and t are independently an integer ranging from 0 to 2, provided that 1≤s+t≤2.

In an exemplary embodiment, $L^3$ and $L^4$ of Chemical Formula 2 may independently be COO, C≡C, or CONK $A^3$ and $A^4$ may be a substituted or unsubstituted benzene ring, and s and t may independently be an integer ranging from 0 to 2, provided that 1≤s+t≤2.

In an exemplary embodiment, the monomer represented by Chemical Formula 1 may not include a halogen atom.

The monomer represented by Chemical Formula 1 may be represented by Chemical Formula 3:

Chemical Formula 3

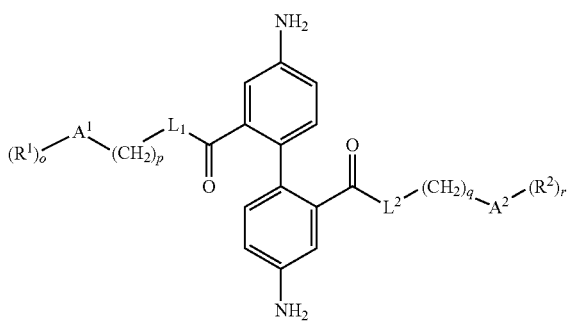

wherein, in Chemical Formula 3, $L^1$, $L^2$, $A^1$, $A^2$, $R^1$, $R^2$, o, p, q, and r are the same as defined in Chemical Formula 1.

In an exemplary embodiment, $L^1$ and $L^2$ of Chemical Formula 3 may independently be O or NH, and for example, $L^1$ and $L^2$ may be all O or $L^1$ and $L^2$ may be all NH, A$^1$ and A$^2$ may independently be a C6 to C20 aromatic ring group, for example, an aromatic ring group selected from benzene, naphthalene, anthracene, and pentalene, or a C3 to C20 hetero aromatic ring group wherein at least one carbon is replaced by at least one of nitrogen and sulfur, for example, pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine, and p and q may independently be an integer ranging from 1 to 6, for example, p and q may independently be an integer ranging from 1 to 3, for example 1 or 2, and in an exemplary embodiment, p and q may be 1.

In an exemplary embodiment, o and r of Chemical Formula 3 may independently be an integer ranging from 0 to 2, for example, o and r may independently be 0 or 1, and in an exemplary embodiment, o and r may be all 0 or may be all 1.

In an exemplary embodiment, R$^1$ and R$^2$ of Chemical Formula 3 may independently be hydrogen, a C1 to C10 alkyl group, for example, one of a methyl group, an ethyl group, a propyl group, a butyl group, a pentyl group, a hexyl group, a heptyl group, an octyl group, a nonyl group, and a decyl group, for example, an iso-propyl group, or a tertiary butyl group (t-butyl group), a C6 to C10 aryl group, for example, a phenyl group or a naphthyl group, a C1 to C10 alkoxy group, for example, a methoxy group, an ethoxy group, or a propoxy group, a halogen, for example, a fluoro group, a nitro group, —CO—NR'R" (wherein, R' and R" are independently hydrogen, a C1 to C20 alkyl group, a C6 to C20 aryl group, or a C7 to C20 arylalkyl group), or a group represented by Chemical Formula 2:

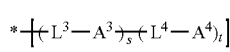

Chemical Formula 2 wherein, in Chemical Formula 2,
L$^3$ and L$^4$ may independently be O, CO, COO, C≡C, or CONN, for example, COO, CEC, or CONN,
A$^3$ and A$^4$ may independently be a substituted or unsubstituted C6 to C20 aromatic ring, for example, a substituted or unsubstituted aromatic ring selected from substituted or unsubstituted benzene, substituted or unsubstituted naphthalene, substituted or unsubstituted anthracene, and substituted or unsubstituted pentalene, or a substituted or unsubstituted C2 to C30 hetero aromatic ring wherein at least one carbon is replaced by at least one of nitrogen and sulfur, for example, substituted or unsubstituted pyrazole, substituted or unsubstituted imidazole, substituted or unsubstituted thiazole, substituted or unsubstituted substituted or unsubstituted triazole, substituted or unsubstituted pyridine, substituted or unsubstituted pyridazine, substituted or unsubstituted pyrimidine, substituted or unsubstituted pyrazine, substituted or unsubstituted triazine, substituted or unsubstituted indazole, substituted or unsubstituted indolizine, substituted or unsubstituted benzimidazole, substituted or unsubstituted benzothiazole, substituted or unsubstituted benzothiophene, substituted or unsubstituted benzopurine, substituted or unsubstituted isoquinoline, or substituted or unsubstituted purine, and for example, A$^3$ and A$^4$ may be a substituted or unsubstituted benzene ring.

In an exemplary embodiment, s and t may independently be an integer ranging from 0 to 2, provided that 1≤s+t≤2.

In Chemical Formula 3,
L$^1$ and L$^2$ may independently be O or NH,
A$^1$ and A$^2$ may independently be selected from benzene, naphthalene, or benzothiazole,
p and q may independently be 1 or 2,
and r may independently be 0 or 1, and
R$^1$ and R$^2$ may independently be hydrogen, an iso-propyl group, a t-butyl group, a methoxy group, an ethoxy group, a fluorine group, a nitro group, —CO—NR'R" (wherein, R' and R" are independently hydrogen, a C1 to C20 alkyl group or a C6 to C20 aryl group), or a group represented by Chemical Formula 2:

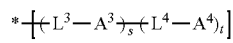

Chemical Formula 2 wherein, in Chemical Formula 2,
L$^3$ and L$^4$ may independently be COO, C≡C, or CONN,
A$^3$ and A$^4$ may be a benzene ring, and
s and t may independently be an integer ranging from 0 to 2, provided that 1≤s+t≤2.

In an exemplary embodiment, the monomer represented by Chemical Formula 3 may not include a halogen atom.

Examples of the monomer, according to an embodiment, may be compounds represented by Compounds M-1 to M-11, but are not limited thereto:

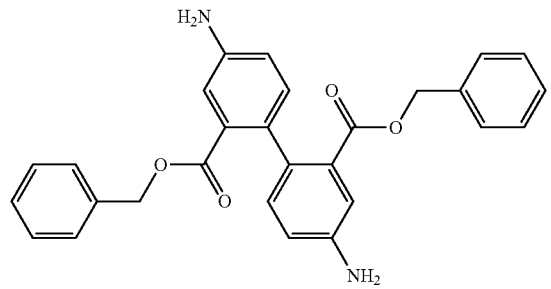

Compound M-1

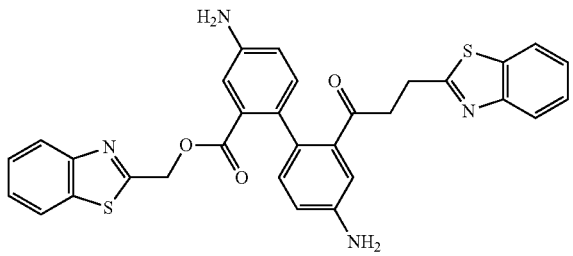

Compound M-2

Compound M-3
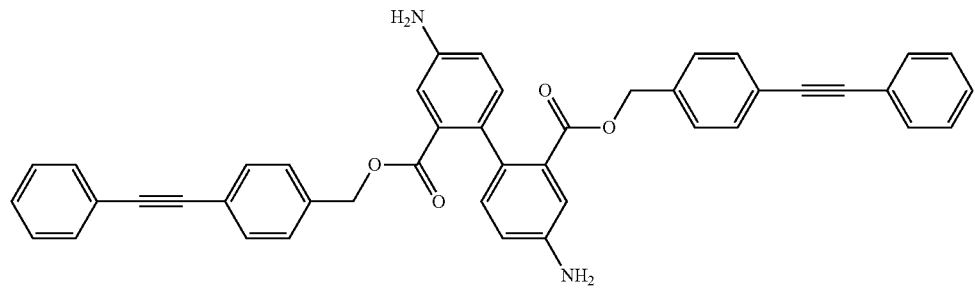
Compound M-4
Compound M-5
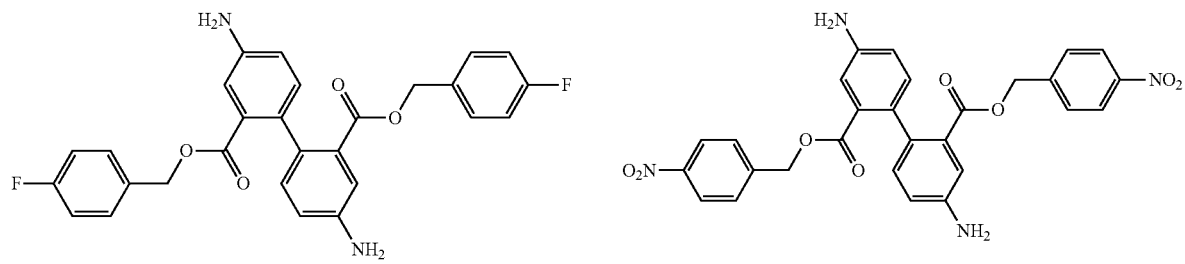
Compound M-6
Compound M-7
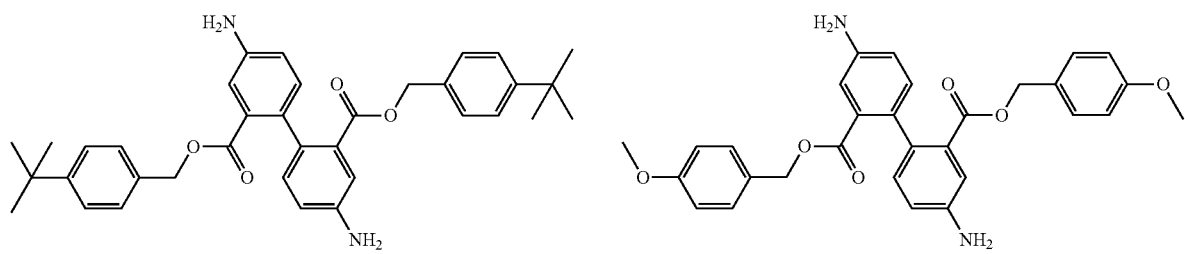
Compound M-8
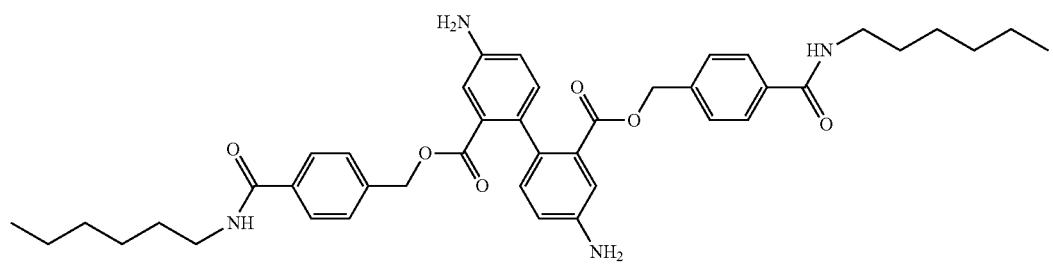
Compound M-9
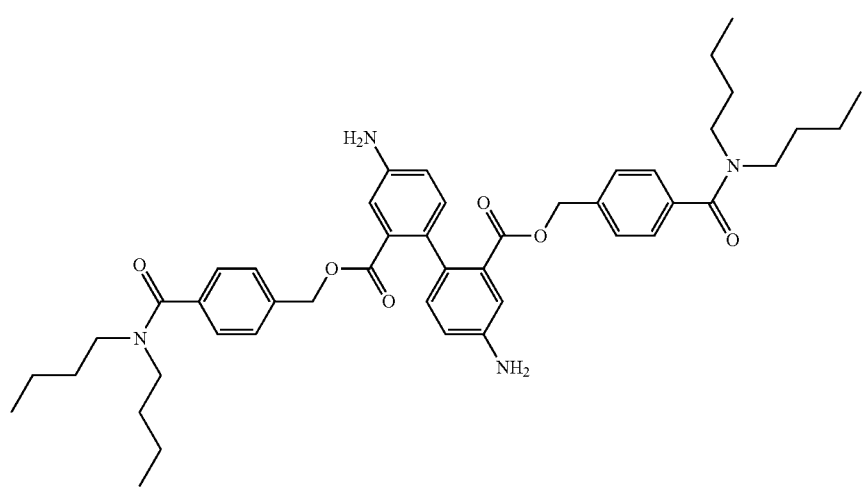

Compound M-10
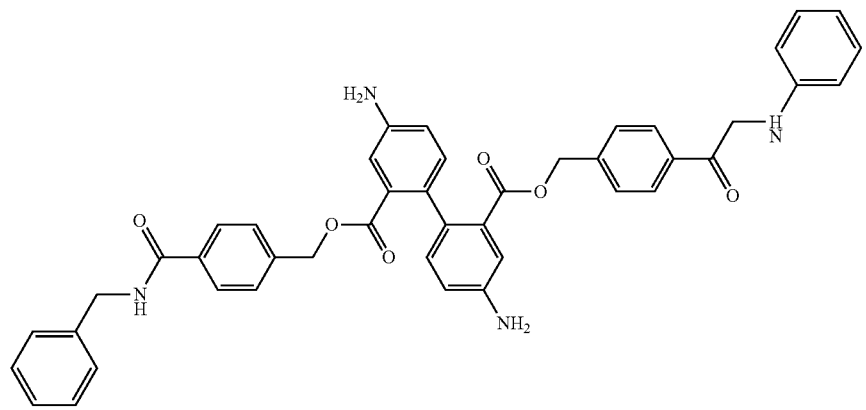
Compound M-11
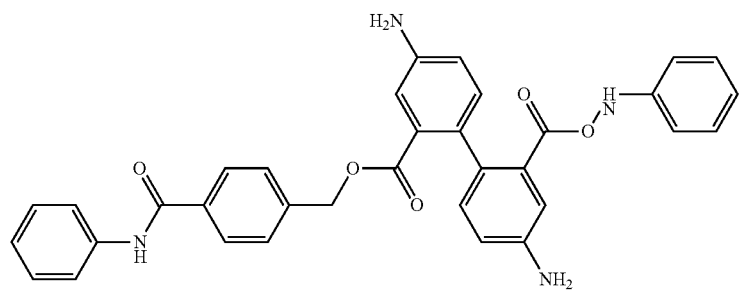
In an exemplary embodiment, among the monomers represented by Chemical Formula 3, a compound wherein $L^1$ and $L^2$ are O, and p and q are 1 may be prepared according to Reaction Scheme 1:
Reaction Scheme 1
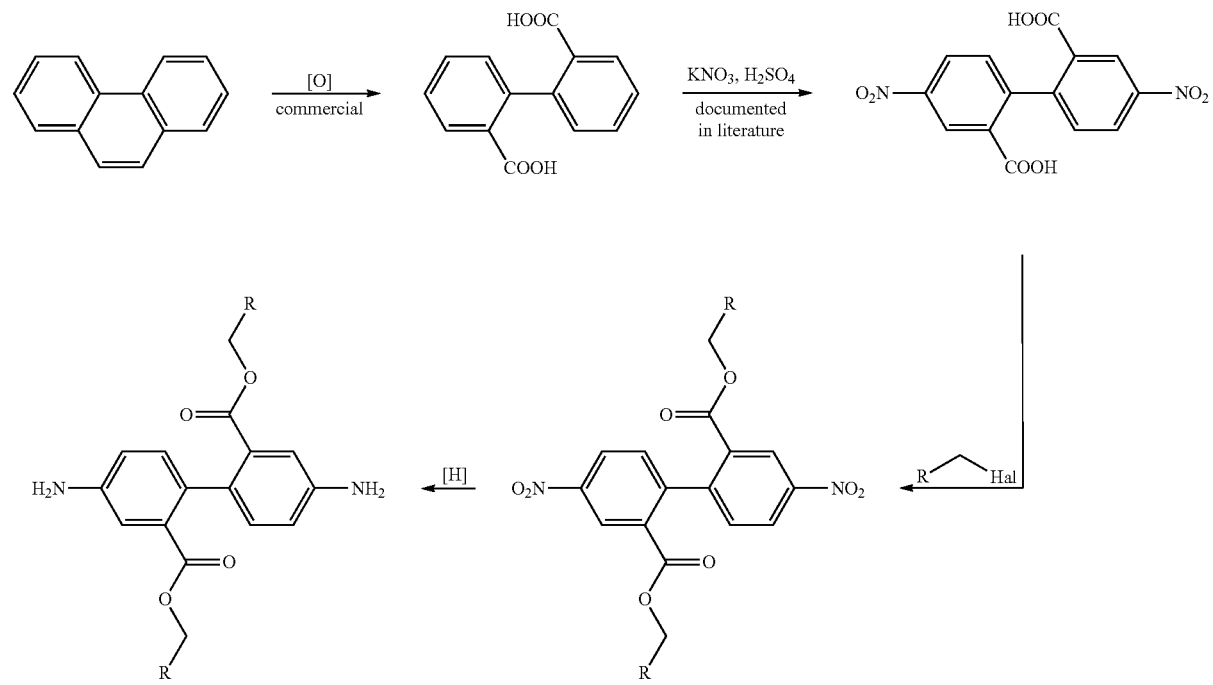

wherein, in Reaction Scheme 1, "R—" corresponds to moieties represented by "$(R^1)_o$-$A^1$-" and "$(R^2)_r$-$A^2$-" in Chemical Formula 3 and "Hal" refers to a halogen atom, for example, F, Cl, Br, I, and the like.

As shown in Reaction Scheme 1, the monomer, according to an embodiment, may be easily prepared according to Reaction Scheme by using commercially available inexpensive starting materials by a person having an ordinary skill in this art.

The monomer is a diamine compound having amino groups at both ends, and accordingly, reacts with a dianhydride compound in the same mole amount to form a polyimide or reacts with a dicarboxylic acid derivative in the same mole amount to form a polyamide. Or, 1 mole of the monomer reacts with 1 mole of a sum of the dianhydride and the dicarboxylic acid derivative to form a poly(amide-imide) copolymer.

Accordingly, in another embodiment, a polymer, a product of reactants including the monomer according to the embodiment and a dianhydride is provided.

The dianhydride that reacts with the monomer in order to prepare the polyimide may be represented by Chemical Formula 4-1 and/or Chemical Formula 4-2:

Chemical Formula 4-1

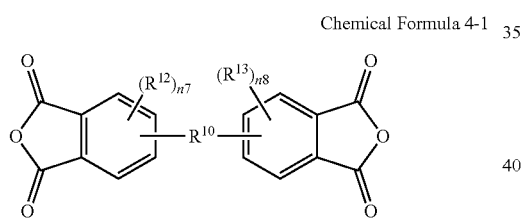

wherein in Chemical Formula 4-1, $R^{10}$ is a single bond, —O—, —S—, —C(=O)—, —CH(OH)—, —C(=O)NH—, —S(=O)$_2$—, —Si(CH$_3$)$_2$—, —(CH$_2$)$_p$—, —(CF$_2$)$_q$—, —C(C$_n$H$_{2n+1}$)$_2$—, —C(C$_n$F$_{2n+1}$)$_2$—, —(CH$_2$)$_p$—C(C$_n$H$_{2n+1}$)$_2$—(CH$_2$)$_q$—, or —(CH$_2$)$_p$—C(C$_n$F$_{2n+1}$)$_2$—(CH$_2$)$_q$— (wherein 1≤n≤10, 1≤p≤10, and 1≤q≤10), $R^{12}$ and $R^{13}$ are independently a halogen, a hydroxy group, a substituted or unsubstituted C1 to C10 aliphatic organic group, a substituted or unsubstituted C6 to C20 aromatic organic group, a —OR$^{201}$ group (wherein R$^{201}$ is a C1 to C10 aliphatic organic group), or a —SiR$^{210}$R$^{211}$R$^{212}$, group (wherein R$^{210}$, R$^{211}$, and R$^{212}$ are independently hydrogen or a C1 to C10 aliphatic organic group), and n7 and n8 are independently one of integers of 0 to 3;

Chemical Formula 4-2

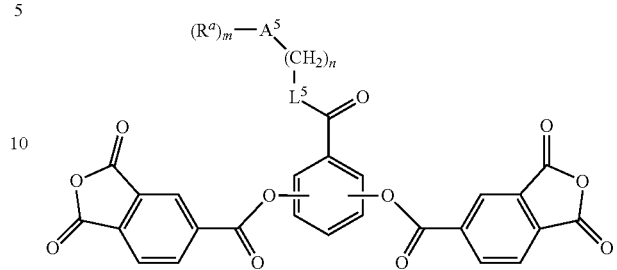

wherein, in Chemical Formula 4-2, $L^5$ is O or NR$^b$ (wherein, R$^b$ is hydrogen or a C1 to C20 alkyl group), $A^5$ is a C6 to C30 aromatic ring, for example, a benzene or naphthalene ring, and $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R", —CO—NR'R", —SiR'R"R'" (wherein R', R", and R'" are independently hydrogen, a C1 to C30 alkyl group, a C6 to C30 aryl group, or a C7 to C30 arylalkyl group), or a group represented by Chemical Formula A:

Chemical Formula A

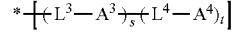

wherein, in Chemical Formula A, $L^3$ and $L^4$ are independently O, CO, COO, C≡C, or CONR$^b$ (wherein, R$^b$ is hydrogen or a C1 to C30 alkyl group), $A^3$ and $A^4$ are independently a substituted or unsubstituted C6 to C30 aromatic ring, for example, a substituted or unsubstituted benzene or naphthalene ring, a substituted or unsubstituted fluorene ring, or a substituted or unsubstituted C7 to C30 arylalkyl group, q and r are independently an integer ranging from 0 to 3, for example, an integer ranging from 0 to 2, provided that 1≤q+r≤2, m of Chemical Formula 4-2 is an integer ranging from 0 to 3, for example, an integer ranging from 0 to 2, for example, 0 or 1, and n is an integer ranging from 0 to 20, for example, an integer ranging from 0 to 10, for example, an integer ranging from 1 to 6, for example, 1 or 2.

A polymer prepared by reacting the monomer, according to an embodiment, with the dianhydride represented by Chemical Formula 4-1 may include a first imide structural unit represented by Chemical Formula 12-1:

Chemical Formula 12-1

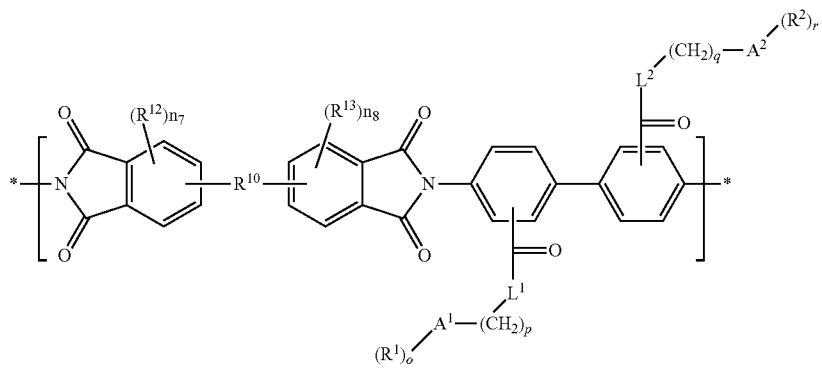

wherein, in Chemical Formula 12-1, $R^1$, $R^2$, $A^1$, $A^2$, $L^1$, $L^2$, o, p, q, and r are the same as defined in Chemical Formula 1, and $R^{10}$, $R^{12}$, $R^{13}$, n7, and n8 are the same as defined in Chemical Formula 4-1.

A polymer prepared by reacting the monomer, according to an embodiment, with the dianhydride represented by Chemical Formula 4-2 may include a second imide structural unit represented by Chemical Formula 12-2:

Chemical Formula 12-2

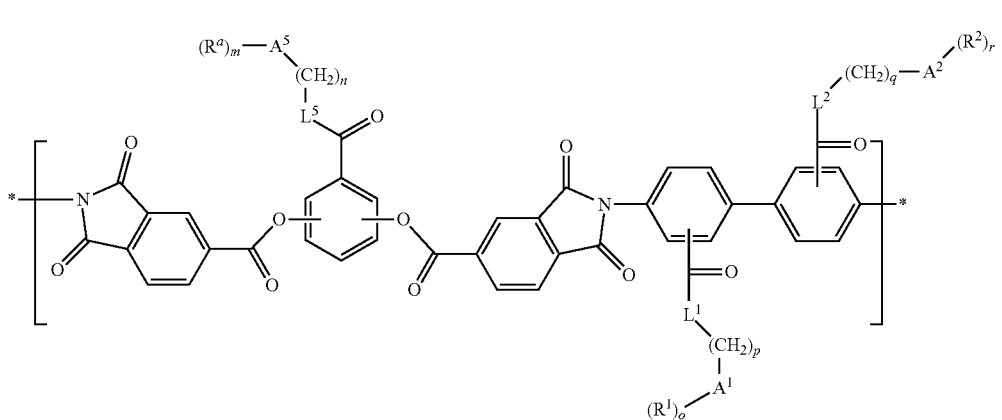

wherein, in Chemical Formula 12-2, $R^1$, $R^2$, $A^1$, $A^2$, $L^1$, $L^2$, o, p, q, and r are the same as defined in Chemical Formula 1, and $L^5$, $A^5$, $R^a$, m, and n are the same as defined in Chemical Formula 4-2.

When the monomer, according to an embodiment, is the monomer represented by Chemical Formula 3, the first imide structural unit may be represented by Chemical Formula 13-1:

Chemical Formula 13-1

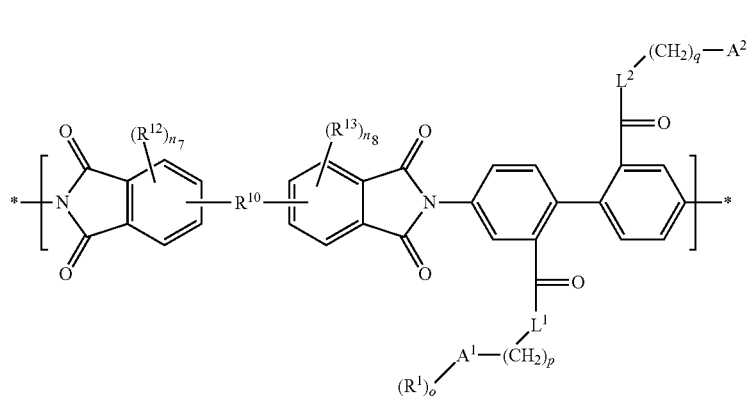

wherein, in Chemical Formula 13-1, $R^1$, $R^2$, $A^1$, $A^2$, $L^1$, $L^2$, o, p, q, and r are the same as defined in Chemical Formula 1, and $R^{10}$, $R^{12}$, $R^{13}$, n7, and n8 are the same as defined in Chemical Formula 4-1.

The dianhydride represented by Chemical Formula 4-1 may include dianhydride represented by Chemical Formula 5-1, dianhydride represented by Chemical Formula 6-1, or a combination thereof:

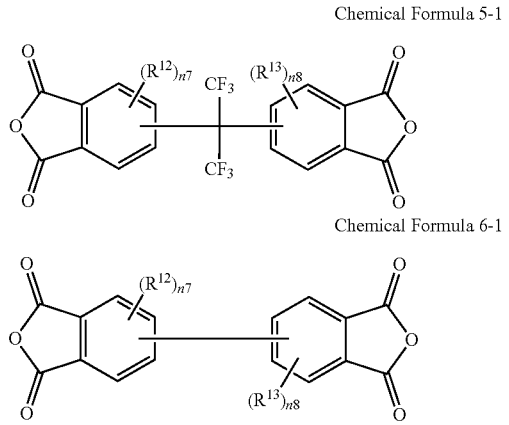

Chemical Formula 5-1

Chemical Formula 6-1 wherein, in Chemical Formula 5-1 and Chemical Formula 6-1, $R^{12}$ and $R^{13}$ are the same or different and are independently a halogen, a hydroxy group, an alkoxy group (—$OR^{208}$, wherein $R^{208}$ is a C1 to C10 aliphatic organic group), a silyl group (—$SiR^{209}R^{210}R^{211}$, wherein $R^{209}$, $R^{210}$, and $R^{211}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n7 and n8 are independently an integer ranging from 0 to 3.

When the polymer, according to an embodiment, is prepared by reacting the monomer represented by Chemical Formula 1 with the dianhydride represented by Chemical Formula 5, the first imide structural unit may include a structural unit represented by Chemical Formula 14-1:

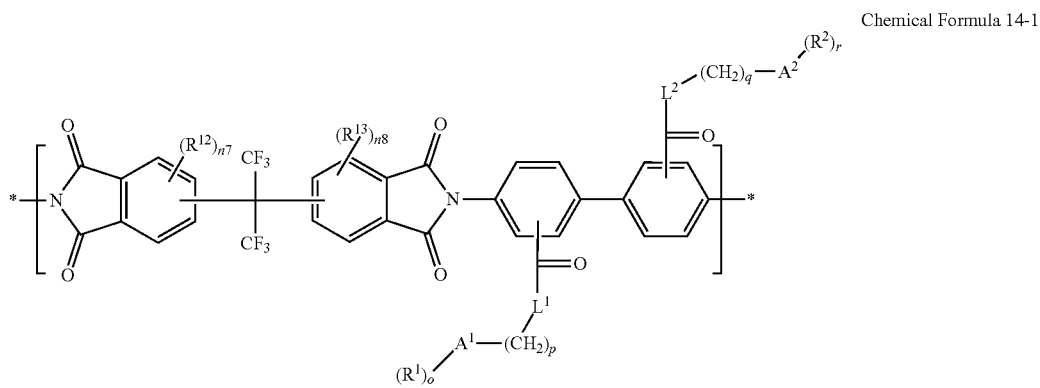

Chemical Formula 14-1 wherein, in Chemical Formula 14-1, $R^1$, $R^2$, $A^1$, $A^2$, $L^2$, o, p, q, and r are the same as defined in Chemical Formula 1, and $R^{12}$, $R^{13}$, n7, and n8 are the same as defined in Chemical Formula.

When the polymer, according to an embodiment, is prepared by reacting the monomer represented by Chemical Formula 1 with the dianhydride represented by Chemical Formula 6-1, the first imide structural unit may include a structural unit represented by Chemical Formula 15-1:

Chemical Formula 15-1

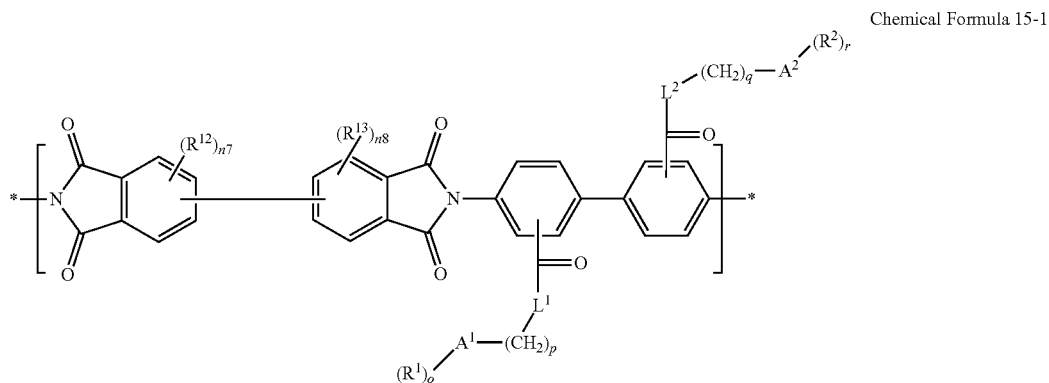

wherein, in Chemical Formula 15-1, $R^1$, $R^2$, $A^1$, $A^2$, $L^2$, o, p, q, and r are the same as defined in Chemical Formula 1, and $R^{12}$, $R^{13}$, n7, and n8 are the same as defined in Chemical Formula 6-1.

When the monomer, according to an embodiment, is the monomer represented by Chemical Formula 3, the second imide structural unit may be represented by Chemical Formula 13-2:

Chemical Formula 13-2

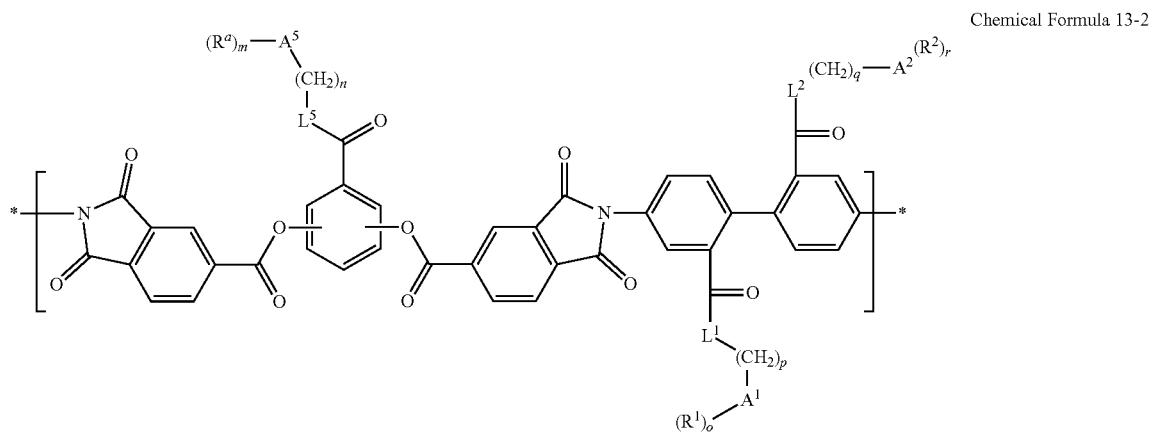

wherein, in Chemical Formula 13-2, $R^1$, $R^2$, $A^1$, $A^2$, $L^1$, $L^2$, o, p, q, and r are the same as defined in Chemical Formula 1, and $L^5$, $A^5$, $R^a$, m, and n are the same as defined in Chemical Formula 4-2.

The dianhydride represented by Chemical Formula 4-2 may include dianhydride represented by Chemical Formula 5-2, dianhydride represented by Chemical Formula 6-2, or a combination thereof:

Chemical Formula 5-2

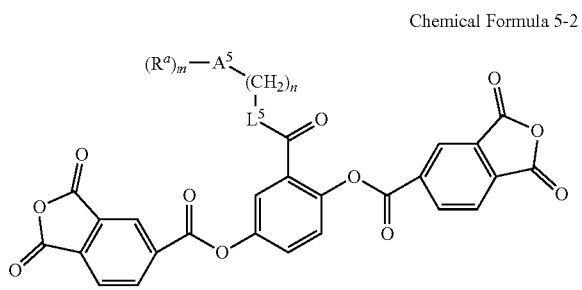

-continued

Chemical Formula 6-2

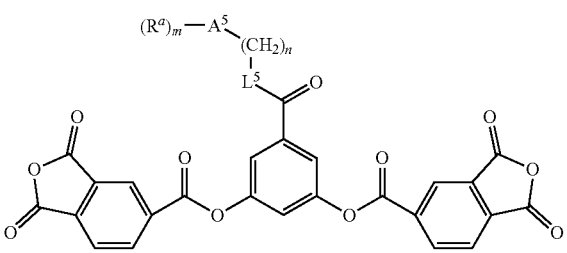

wherein, in Chemical Formula 5-2 and Chemical Formula 6-2, $L^5$, $A^5$, $R^a$, m, and n are the same as defined in Chemical Formula 4-2.

When the polymer, according to an embodiment, is prepared by reacting the monomer represented by Chemical Formula 1 with the dianhydride represented by Chemical Formula 5-2, the second imide structural unit may include a structural unit represented by Chemical Formula 14-2:

Chemical Formula 14-2

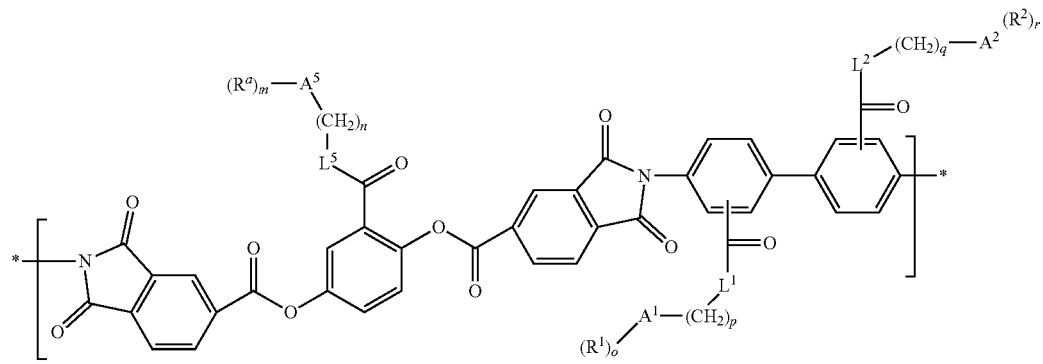

wherein, in Chemical Formula 14-2, $R^1$, $R^2$, $A^1$, $A^2$, $L^1$, $L^2$, o, p, q, and r are the same as defined in Chemical Formula 1, and $L^5$, $A^5$, $R^a$, m, and n are the same as defined in Chemical Formula 4-2.

When the polymer, according to an embodiment, is prepared by reacting the monomer represented by Chemical Formula 1 with the dianhydride represented by Chemical Formula 6-2, the second imide structural unit may include a structural unit represented by Chemical Formula 15-2:

Chemical Formula 15-2

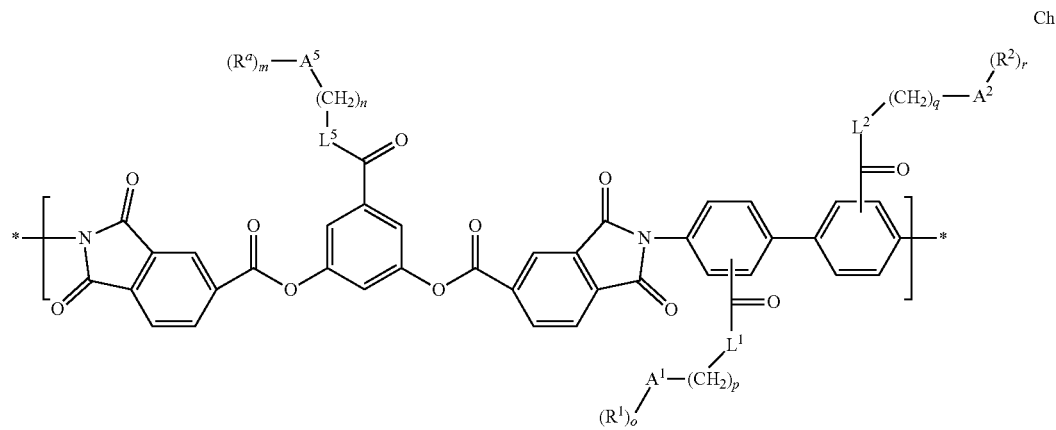

wherein, in Chemical Formula 15-2, $R^1$, $R^2$, $A^1$, $A^2$, $L^1$, $L^2$, o, p, q, and r are the same as defined in Chemical Formula 1, and $L^5$, $A^5$, $R^a$, m, and n are the same as defined in Chemical Formula 4-2.

In another embodiment, a polymer is a product of reactants including the monomer according to the embodiment and a dicarboxylic acid derivative. The polymer may be polyamide.

The dicarboxylic acid derivative to provide the polyamide may be represented by Chemical Formula 7:

Chemical Formula 7

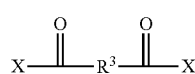

wherein, in Chemical Formula 7, $R^3$ is at least one of a substituted or unsubstituted phenylene group and a substituted or unsubstituted biphenylene group, and each of X is the same or different and is a halogen atom.

In Chemical Formula 7, $R^3$ may be at least one of an unsubstituted phenylene group and an unsubstituted biphenylene group, and X may independently be Cl or Br.

Polyamide prepared from the monomer represented by Chemical Formula 1, according to an embodiment, and the dicarboxylic acid derivative represented by Chemical Formula 7 may include a first amide structural unit represented by Chemical Formula 16:

Chemical Formula 16

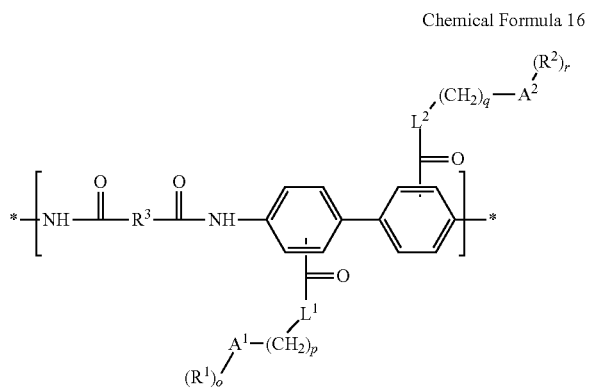

wherein, in Chemical Formula 16, $R^1$, $R^2$, $A^1$, $A^2$, $L^1$, $L^2$, o, p, q, and r are the same as defined in Chemical Formula 1, and $R^3$ is the same as defined in Chemical Formula 7.

In an exemplary embodiment, when the monomer represented by Chemical Formula 1 is the diamine represented by Chemical Formula 3, Chemical Formula 16 may be represented by Chemical Formula 17:

Chemical Formula 17

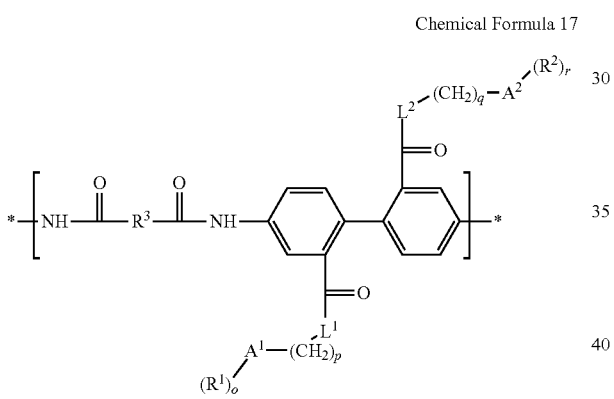

wherein, in Chemical Formula 17, $R^1$, $R^2$, $A^1$, $A^2$, $L^1$, $L^2$, o, p, q, and r are the same as defined in Chemical Formula 1 and $R^3$ is the same as defined in Chemical Formula 7.

$R^3$ of Chemical Formula 17 may be an unsubstituted phenylene group or an unsubstituted biphenylene group, and when $R^3$ is an unsubstituted phenylene group, the amide structural unit represented by Chemical Formula 17 may be represented by Chemical Formula 18 or Chemical Formula 19:

Chemical Formula 18

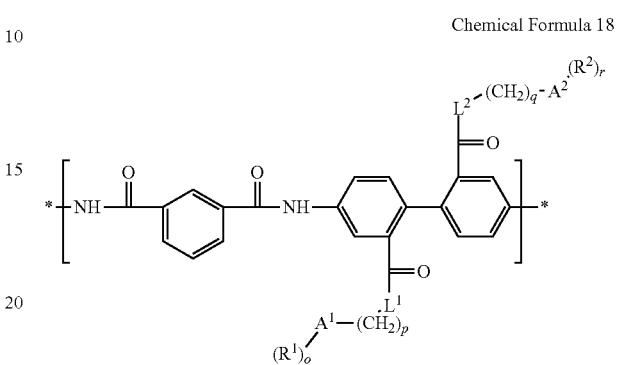

Chemical Formula 19

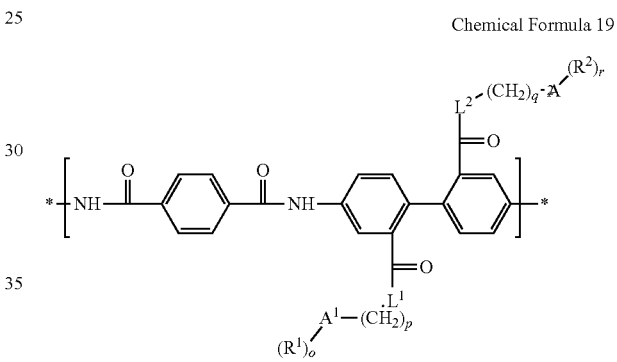

In Chemical Formula 18 and Chemical Formula 19, $R^1$, $R^2$, $A^1$, $A^2$, $L^1$, $L^2$, o, p, q, and r are the same as defined in Chemical Formula 1.

When $R^3$ of Chemical Formula 17 is an unsubstituted biphenylene group, the amide structural unit represented by Chemical Formula 17 may be represented by Chemical Formula 20 or Chemical Formula 21:

Chemical Formula 20

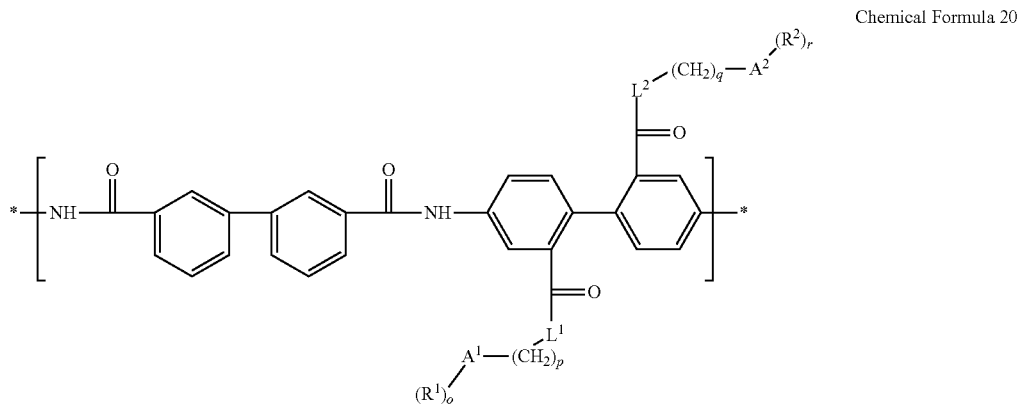

-continued

Chemical Formula 21

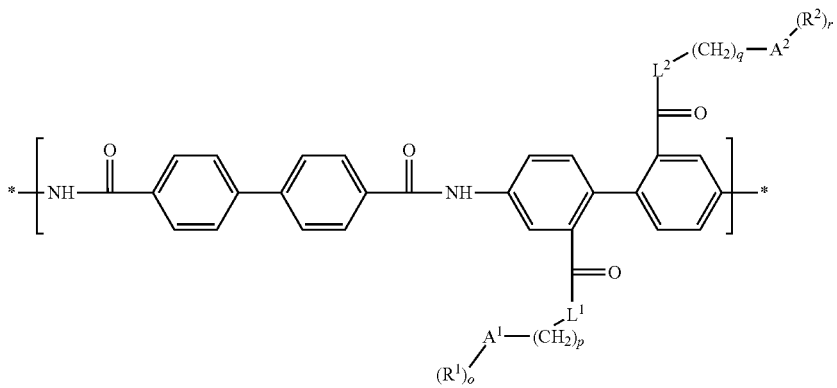

In Chemical Formula 20 and Chemical Formula 21, $R^1$, $R^2$, $A^1$, $A^2$, $L^1$, $L^2$, o, p, q, and r are the same as defined in Chemical Formula 1.

The polymer may be a polymer that is a polymerization product of reactants including the monomer represented by Chemical Formula 1, according to an embodiment, a dianhydride, and a dicarboxylic acid derivative and may be a poly(amide-imide) copolymer. The poly(amide-imide) copolymer may include at least one of the first imide structural unit and the second imide structural unit, and the first amide structural unit.

In an exemplary embodiment, the polymer may be a product of reactants further including diamine represented by Chemical Formula 8 in addition to the diamine represented by Chemical Formula 1, according to an embodiment:

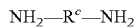 Chemical Formula 8 wherein, in Chemical Formula 8,
$R^c$ is a substituted or unsubstituted C6 to C30 aromatic organic group, wherein the substituted or unsubstituted C6 to C30 aromatic organic group is present as a substituted or unsubstituted single aromatic ring; a fused ring including two or more substituted or unsubstituted aromatic rings; or a ring system including two or more of the substituted or unsubstituted single aromatic ring and/or the fused ring that are linked by a single bond, or a functional group of a fluorenylene group, a substituted or unsubstituted C1 to C10 cycloalkylene group, a substituted or unsubstituted C6 to C15 arylene group, —O—, —S—, —C(=O)—, —CH(OH)—, —S(=O)$_2$—, —Si(CH$_3$)$_2$—, —(CH$_2$)$_p$— (wherein, 1≤q≤10), —(CF$_2$)$_q$— (wherein, 1≤q≤10), —C(CH$_3$)$_2$—, —C(CF$_3$)$_2$—, —C(=O)NH—, or a combination thereof.

The diamine represented by Chemical Formula 8 may be represented by at least one of Chemical Formula 9 to Chemical Formula 11:

wherein, in Chemical Formula 9,
$R^d$ is selected from the following chemical formulae:

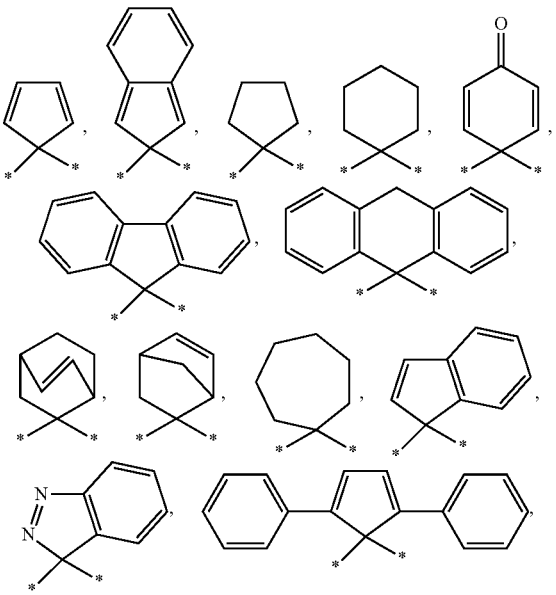

$R^7$ and $R^8$ are the same or different and are independently a halogen, a hydroxy group, an alkoxy group (—OR$^{200}$, wherein R$^{200}$ is a C1 to C10 aliphatic organic group), a silyl group (—SiR$^{201}$R$^{202}$R$^{203}$, wherein R$^{201}$, R$^{202}$, and R$^{203}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and
n1 and n2 are independently an integer ranging from 0 to 4;

Chemical Formula 9

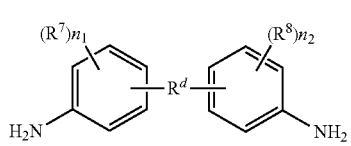

Chemical Formula 10

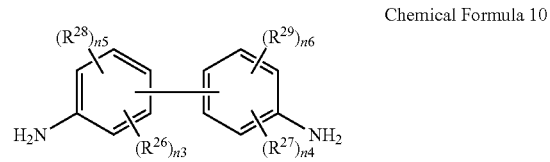

wherein, in Chemical Formula 10,

R$^{26}$ and R$^{27}$ are the same or different and are independently an electron withdrawing group selected from —CF$_3$, —CCl$_3$, —CBr$_3$, —Cl$_3$, —NO$_2$, —CN, —COCH$_3$, or —CO$_2$O$_2$H$_6$, R$^{28}$ and R$^{29}$ are the same or different and are independently a hydroxy group, an alkoxy group (—OR$^{204}$, wherein R$^{204}$ is a C1 to C10 aliphatic organic group), a silyl group (—SiR$^{205}$R$^{206}$R$^{207}$, wherein R$^{206}$, R$^{206}$, and R$^{207}$ are the same or different and are independently hydrogen or a C1 to C10 aliphatic organic group), a substituted or unsubstituted C1 to C10 aliphatic organic group, or a substituted or unsubstituted C6 to C20 aromatic organic group, n3 is an integer ranging from 1 to 4, and n5 is an integer ranging from 0 to 3, provided that n3+n5 is an integer ranging from 1 to 4, and n4 is an integer ranging from 1 to 4, and n6 is an integer ranging from 0 to 3, provided that n4+n6 is an integer ranging from 1 to 4;

Chemical Formula 11

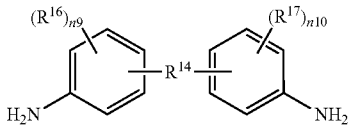

wherein, in Chemical Formula 11,

R$^{14}$ includes O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, C(=O)NH, or a substituted or unsubstituted C6 to C18 aromatic organic group, wherein the substituted or unsubstituted C6 to C18 aromatic organic group is present as a single aromatic ring, a fused ring including two or more aromatic rings, or a ring system including two or more of the single aromatic ring and/or the fused ring that are linked by a single bond or a functional group of a fluorenylene group, O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, or C(=O)NH, R$^{16}$ and R$^{17}$ are the same or different and are independently a halogen, a hydroxy group, an alkoxy group (—OR$^{212}$, wherein R$^{212}$ is a C1 to C10 aliphatic organic group), a silyl group (—SiR$^{213}$R$^{214}$R$^{215}$, wherein R$^{213}$, R$^{214}$, and R$^{215}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n9 and n10 are independently an integer ranging from 0 to 4.

The diamine represented by Chemical Formula 8 may include at least one of the diamine represented by Chemical Formula 10 and the diamine represented by Chemical Formula 11, wherein the diamine represented by Chemical Formula may include 2,2'-bis(trifluoromethyl)benzidine (TFDB), and the diamine represented by Chemical Formula 11 may include 4,4'-diaminodiphenyl sulfone (DADPS).

The diamine represented by Chemical Formula 8 may be included in an amount of less than or equal to about 50 mole percent (mol %), for example, about mol % to about 50 mol %, for example, about 10 mol % to about 50 mol %, for example, about 15 mol % to about 45 mol %, for example, about 20 mol % to about mol %, for example, about 25 mol % to about 45 mol %, for example, about 30 mol % to about 45 mol %, and for example, about 35 mol % to about 45 mol % based on a total amount of the monomer represented by Chemical Formula 1 and the diamine represented by Chemical Formula 8.

When the diamine represented by Chemical Formula 8, for example, at least one of diamine represented by Chemical Formula 9 to Chemical Formula 11, is polymerized with a dianhydride, a dicarboxylic acid derivative, or a combination thereof in addition to the monomer represented by Chemical Formula 1, the polymer may further include a second imide structural unit formed by the diamine represented by Chemical Formula 8, for example, at least one of diamine represented by Chemical Formula 9 to Chemical Formula 11, the dianhydride represented by Chemical Formula 4, for example, the dianhydride represented by Chemical Formula 5 and/or Chemical Formula 6, and may also include a second amide structural unit formed along with the dicarboxylic acid derivative represented by Chemical Formula 7.

The polyimide, polyamide, or the poly(amide-imide) copolymer according to the embodiment may be prepared by a known method in this art by a person having an ordinary skill, which is not limited to a particular method.

A polymer prepared from reactants including the monomer, according to an embodiment, a dianhydride, a dicarboxylic acid derivative, and/or a combination thereof by a known method may be a polymer of polyimide, polyamide, or a poly(amide-imide) copolymer having desirable optical properties and high heat resistance by adjusting ratios of the monomer, dianhydride, and/or dicarboxylic acid.

The polymer may be, for example, formed as a film, and thus, used as a polymer film. The polymer film may be, for example, transparent, and thus, used for any use requiring transparency. The polymer film may be, for example, used for various uses such as a substrate, a protective film, a compensation film, an optical film, a dielectric layer, an insulation layer, an adhesive layer, and the like.

Hereinafter, a compensation film, according to an embodiment, is described.

A compensation film, according to an embodiment, includes the polymer.

That is, the compensation film, according to an embodiment, may include a polyimide-based polymer including an imide structural unit prepared by reacting the monomer, according to an embodiment, that is, the monomer represented by Chemical Formula 1 with dianhydride, for example, a first imide structural unit represented by at least one of Chemical Formulae 12-1, 13-1, 14-1, and 15-1 which is prepared by reacting the monomer represented by Chemical Formula 1 with dianhydride represented by Chemical Formula 4-1.

Or, the compensation film, according to an embodiment, may include a polyimide-based polymer including a second imide structural unit represented by at least one of Chemical Formulae 12-2, 13-2, 14-2 and 15-2 which is prepared by reacting the monomer, according to an embodiment, that is, the monomer represented by Chemical Formula 1 with dianhydride represented by Chemical Formula 4-2.

Or, the compensation film, according to an embodiment, may include a polyimide-based polymer including a first imide structural unit and a second imide structural unit which is prepared by reacting the monomer, according to an embodiment, that is, the monomer represented by Chemical Formula 1 with dianhydride represented by Chemical Formula 4-1 and dianhydride represented by Chemical Formula 4-2.

Or, the compensation film may include a polyimide-based polymer that is product of reactants further including the diamine represented by Chemical Formula 8 as an additional diamine in addition to the monomer represented by Chemical Formula 1, and the polymer may include a polyimide-based polymer that further includes a third imide structural unit and/or a fourth imide structural unit derived from a reaction of the diamine represented by Chemical Formula 8 with dianhydride represented by at least one of Chemical Formula 4-1 and Chemical Formula 4-2, in addition to the first imide structural unit and second imide structural unit.

In addition, the compensation film may include a polyamide-based polymer including a first amide structural unit prepared by reacting the monomer represented by Chemical Formula 1 with the dicarboxylic acid derivative represented by Chemical Formula 7 and represented by Chemical Formulae 16 to 21.

Or, the compensation film may include a polyamide-based polymer that further includes a second amide structural unit produced from a polymerization reaction of the diamine represented by Chemical Formula 8 and the dicarboxylic acid derivative represented by Chemical Formula 7 in addition to the first amide structural unit.

Furthermore, the compensation film may include a poly (amide-imide) copolymer including at least one of the first imide structural unit and the second imide structural unit and the first amide structural unit.

In addition, the compensation film may include a poly (amide-imide) copolymer including a imide structural unit including at least one of a third imide structural unit and a fourth imide structural unit in addition to the first imide structural unit and the second imide structural unit, and at least one of the first amide structural unit and/or the second amide structural unit.

A polymer, according to an embodiment, may include, if necessary, a structural unit that is a reaction product of additional non-limiting monomers, dianhydride, diamine, and/or, dicarboxylic acid derivatives, along with the first imide structural unit and/or second imide structural unit in addition to the structural unit. The additional monomers, dianhydride, diamine and/or dicarboxylic acid derivatives, have no particular limit, but may be used along with any other kinds which may reinforce a function of an article manufactured from a polymer or a copolymer formed thereof, for example, an optical film, for example, a compensation film.

A film formed of the polymer, according to an embodiment, may have high thermal stability, for example, a high glass transition temperature of greater than or equal to about 150° C., for example, greater than or equal to about 160° C., for example, greater than or equal to about 170° C., for example, greater than or equal to about 180° C., for example, greater than or equal to about 190° C., for example, greater than or equal to about 200° C., for example, greater than or equal to about 210° C., for example, greater than or equal to about 220° C., for example, greater than or equal to about 230° C., for example, greater than or equal to about 240° C., and for example, greater than or equal to about 250° C.

In addition, the film formed of the polymer, according to an embodiment, may have excellent optical characteristic, for example, high light transmittance at about 450 nm, for example, transmittance of greater than or equal to about 85%, for example, greater than or equal to about 86%, for example, greater than or equal to about 87%, for example, greater than or equal to about 88%, and for example, greater than or equal to about 89%.

In addition, the film formed of the polymer, according to an embodiment, may have a high out-of-plane birefringence, for example, a retardation of greater than or equal to about 0.005, for example, greater than or equal to about 0.006, for example, greater than or equal to about 0.007, for example, greater than or equal to about 0.008, for example, greater than or equal to about 0.009, and for example, greater than or equal to about 0.010 at a thin film thickness of less than or equal to about 100 micrometers (μm), for example, less than or equal to about 90 μm, for example, less than or equal to about 80 μm, for example, less than or equal to about 70 μm, for example, less than or equal to about 60 μm, for example, less than or equal to about 50 μm, for example, less than or equal to about 40 μm, for example, less than or equal to about 30 μm, for example, less than or equal to about 20 μm.

In other words, the film formed of the polymer, according to an embodiment, shows high thermal stability, for example, a high glass transition temperature and excellent optical characteristics, for example, high light transmittance and high out-of-plane birefringence at 450 nm, particularly, a high out-of-plane birefringence at a thin film thickness of less than or equal to about 100 μm, and thus, may be used as an optical film such as a compensation film and the like.

When the film is used as a compensation film, the compensation film may have a predetermined retardation by changing light absorption characteristics depending on a refractive index and a wavelength.

A retardation (R) of the compensation film may be represented by an in-plane retardation ($R_o$) and a thickness direction retardation ($R_{th}$). The in-plane retardation ($R_o$) of compensation film is a retardation generated in in-plane of the compensation film and may be represented by $R_o=(n_x-n_y)d$. The thickness direction retardation ($R_{th}$) of the compensation film is a retardation generated in a thickness direction of the compensation film and may be represented by $R_{th}=\{[(n_x+n_y)/2]-n_z\}d$. Herein, $n_x$ is a refractive index in a direction having a highest in-plane refractive index in a plane of the compensation film (hereinafter, referred to as a 'slow axis'), $n_y$ is a refractive index in a direction having a lowest in-plane refractive index in a plane of the compensation film (hereinafter, referred to as a 'fast axis'), n, is a refractive index in a direction perpendicular to the slow axis and the fast axis of the compensation film, and d is a thickness of the compensation film.

The compensation film may have predetermined in-plane retardation and thickness direction retardation by changing the $n_x$, $n_y$, $n_z$, and/or thickness (d).

The retardation of the compensation film may be the same or different depending on a wavelength.

For example, the compensation film may have a forward wavelength dispersion retardation wherein a retardation about light at a short wavelength is larger than a retardation about light at a long wavelength. When a 550 nanometers (nm) wavelength is a reference wavelength, for example retardations (R) at 450 nm, 550 nm, and 650 nm wavelengths of the compensation film may satisfy Relationship Equation 1 or 2.

R(450 nm)≥R(550 nm)>R(650 nm)   Relationship Equation 1

R(450 nm)>R(550 nm)≥R(650 nm)   Relationship Equation 2

For example, the compensation film may have a flat wavelength dispersion retardation wherein a retardation about light at a long wavelength is substantially equivalent to a retardation about light at a short wavelength and retardations (R) at 450 nm, 550 nm, and 650 nm wavelengths of the compensation film may satisfy Relationship Equation 3.

$$R(450\ nm)=R(550\ nm)=R(650\ nm) \quad \text{Relationship Equation 3}$$

For example, the compensation film may have a reverse wavelength dispersion retardation wherein a retardation about light at a long wavelength is larger than a retardation about light at a short wavelength and for example retardations (R) at 450 nm, 550 nm, and 650 nm wavelengths of the compensation film may satisfy Relationship Equation 4 or 5.

$$R(450\ nm) \leq R(550\ nm) < R(650\ nm) \quad \text{Relationship Equation 4}$$

$$R(450\ nm) < R(550\ nm) \leq R(650\ nm) \quad \text{Relationship Equation 5}$$

In Relationship Equations 1 to 5,

R(450 nm) is an in-plane retardation or a thickness direction retardation of the compensation film at a 450 nm wavelength, R(550 nm) is an in-plane retardation or a thickness direction retardation of the compensation film at a 550 nm wavelength, and R(650 nm) is an in-plane retardation or a thickness direction retardation of the compensation film at a 650 nm wavelength.

The compensation film may be adjusted to have a desired retardation depending on a wavelength.

The compensation film may have high birefringence, and thus, a relatively thin thickness. The compensation film may have, for example, a thickness of about 1 micrometer (μm) to about 200 μm, within the range, a thickness of about 1 μm to about 150 μm, and within the range, a thickness of about 1 μm to about 100 μm.

The compensation film includes a substantially transparent polymer, and thus, may be used as a substrate, and accordingly, a separate substrate beneath the compensation film may be omitted. Accordingly, a thickness of the compensation film may be further reduced. Accordingly, the compensation film may be effectively applied to a flexible display device such as a foldable display device or a bendable display device, and thus, improve optical properties and display characteristics.

The compensation film may be formed, for example, through preparation of the monomer, according to an embodiment, polymerization of the monomer into a polymer, formation of the polymer into a polymer film, and elongation of the polymer film.

The compensation film may be elongated, for example, at an elongation rate of about 110% to about 1,000% at about 50° C. to about 500° C. Herein, the elongation rate indicates a length ratio before and after the elongation, that is, an increased length degree of the compensation film after elongation in a uniaxial direction. For example, the compensation film may be elongated in a uniaxial direction.

The compensation film may be prepared by a method including, for example, preparing a monomer, according to an embodiment, preparing a polymer by polymerizing the monomer, solvating or dispersing the polymer in a solvent to prepare a polymer solution or dispersion, forming a thin film by coating the polymer solution or dispersion on a substrate, and heating the thin film.

The compensation film may be used alone or along with other compensation films.

The compensation film may be used with a polarizer and may be used as an optical film to prevent reflection of external light of a display device. The optical film may be for example an anti-reflective film, but is not limited thereto.

Figure 2:
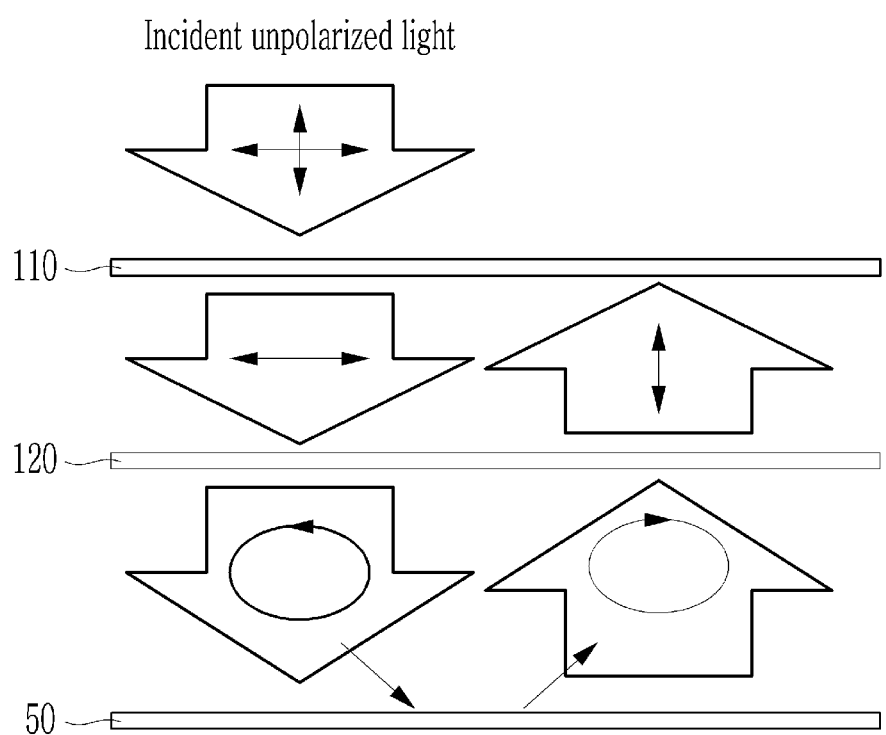
FIG. 2 is a schematic cross-sectional view showing the external light anti-reflection principle of an optical film.
Figure 3:
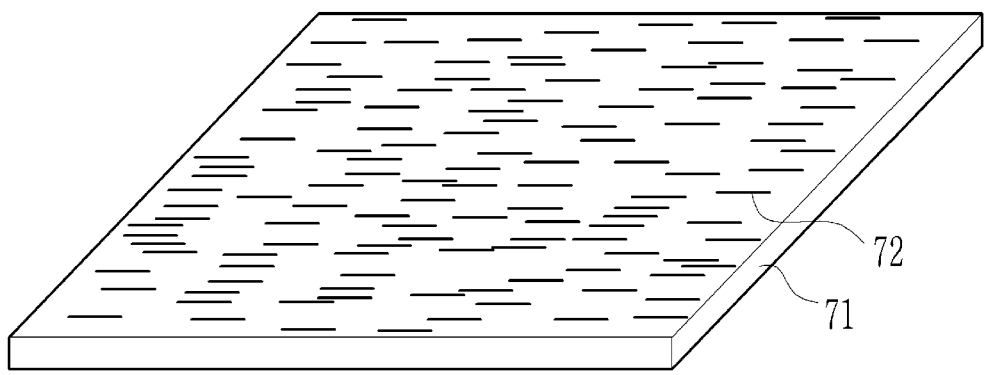
FIG. 3 is a schematic view showing an embodiment of a polarizing film.

FIG. 1 is a schematic cross-sectional view of an optical film, according to an embodiment, FIG. 2 is a schematic view showing the external light anti-reflection principle of an optical film, and FIG. 3 is a schematic view showing an embodiment of a polarizing film.

Referring to FIG. 1, an optical film 100, according to an embodiment, includes a polarizer 110 and a compensation film 120. The compensation film 120 may circularly polarize light passing the polarizer 110 to generate retardation and may have an effect on reflection and/or absorption of light.

For example, the optical film 100 may be formed on one surface or both surfaces of a display device and particularly on the screen side of the display device, and thus, may prevent reflection of light inflowing from the outside (hereinafter referred to as "external light"). Accordingly, visibility deterioration due to reflection of external light may be prevented.

FIG. 2 is a schematic view showing the external light anti-reflection principle of an optical film.

Referring to FIG. 2, while the incident unpolarized light having entered from the outside is passed through the polarizer 110, only a first polarized perpendicular component, which is one polarized perpendicular component of two polarized perpendicular components, is transmitted, and the polarized light is shifted into circularly polarized light by passing through the compensation film 120. While the circularly polarized light is reflected in a display panel 50 including a substrate, an electrode, and so on, and changes to the circular polarization direction, and the circularly polarized light is passed through the compensation film 120 again, only a second polarized perpendicular component, which is the other polarized perpendicular component of the two polarized perpendicular components, may be transmitted. As the second polarized perpendicular component is not passed through the polarizer 110, and light does not exit to the outside, effects of preventing the external light reflection may be provided.

The polarizer 110 may be for example a polarizing plate or a polarizing film.

The polarizer 110 may be, for example, a PVA polarizer that includes polyvinylalcohol.

Referring to FIG. 3, the polarizer 110 may be a polarizing film having an integral structure that is made of for example a melt blend of a polymer resin 71 and a dichroic dye 72.

The polymer resin 71 may be for example a hydrophobic polymer resin, for example polyolefin such as polyethylene (PE), polypropylene (PP) and a copolymer thereof; polyamide such as nylon and aromatic polyamide, polyester such as polyethylene terephthalate (PET), polyethyleneterephthalate glycole (PETG), and polyethylenenaphthalate (PEN); polyacrylate such as polymethyl(meth)acrylate; polystyrene such as polystyrene (PS) and an acrylonitrile-styrene copolymer; polycarbonate; a vinyl chloride-based resin; polyimide; a sulfone resin; polyethersulfone; polyether-etherketone; polyphenylene sulfide; a polyvinyl alcohol resin; a vinylidene chloride resin; a polyvinyl butyral resin; an allylate resin; polyoxymethylene; epoxy resin, a copolymer thereof, or a combination thereof.

Among them, the polymer resin 71 may be for example a polyolefin resin, a polyamide resin, a polyester resin, a polyacrylic resin, a polystyrene resin, a copolymer thereof, or a combination thereof, for example polyethylene (PE), polypropylene (PP), polyethylene terephthalate (PET), polyethylene terephthalate glycole (PETG), polyethylene naphthalate (PEN), nylon, a copolymer thereof, or a combination thereof.

Among them, the polymer resin 71 may be polyolefin. The polyolefin may be for example a mixture of at least two selected from polyethylene (PE), polypropylene (PP), a copolymer of polyethylene and polypropylene (PE-PP), and may be for example a mixture of polypropylene (PP) and a polyethylene-polypropylene copolymer (PE-PP).

The polymer resin 71 may have transmittance of greater than or equal to about 85% in a wavelength region of about 400 nm to 780 nm. The polymer resin 71 may be elongated in a uniaxial direction. The uniaxial direction may be the same as a length direction of the dichroic dye 72 that will be described later.

The dichroic dye 72 is dispersed in the polymer resin 71 and aligned in one direction along the elongation direction of the polymer resin 71. The dichroic dye 72 transmits one perpendicular polarization component out of two perpendicular polarization components in a predetermined wavelength region.

The dichroic dye 72 may be included in an amount of about 0.01 to about parts by weight based on 100 parts by weight of the polymer resin 71. Within the range, sufficient polarization characteristics may be obtained without deteriorating transmittance of a polarization film. Within the above range, the dichroic dye 72 may be included in an amount of about 0.05 to about 1 part by weight based on 100 parts by weight of the polymer resin 71.

The polarizer 110 may have a relatively thin thickness of less than or equal to about 100 μm, for example, about 30 μm to about 95 μm. When the polarizing film 70 has a thickness with the range, the polarizer 110 is relatively thinner than a polyvinyl alcohol polarizing plate requiring a protective layer such as triacetyl cellulose (TAC), and thus, may realize a thin display device.

The compensation film 120 is the same as described above.

The optical film 100 may further include a correction layer (not shown) disposed on one surface of the compensation film 120. The correction layer may be for example a color shift resistant layer, but is not limited thereto.

The optical film 100 may further include a light blocking layer (not shown) extended along the edge. The light blocking layer may be extended along the circumference of the optical film 100 and may be for example disposed between the polarizer 110 and the compensation film 120. The light blocking layer may include an opaque material, for example, a black material. For example, the light blocking layer may be made of a black ink.

The optical film 100 may be applied to various display devices.

A display device, according to an embodiment, includes a display panel and an optical film disposed on one surface of the display panel. The display panel may be a liquid crystal panel or an organic light emitting panel, but is not limited thereto.

Hereinafter, for one example of the display device, an organic light emitting diode (OLED) display is described.

Figure 4:
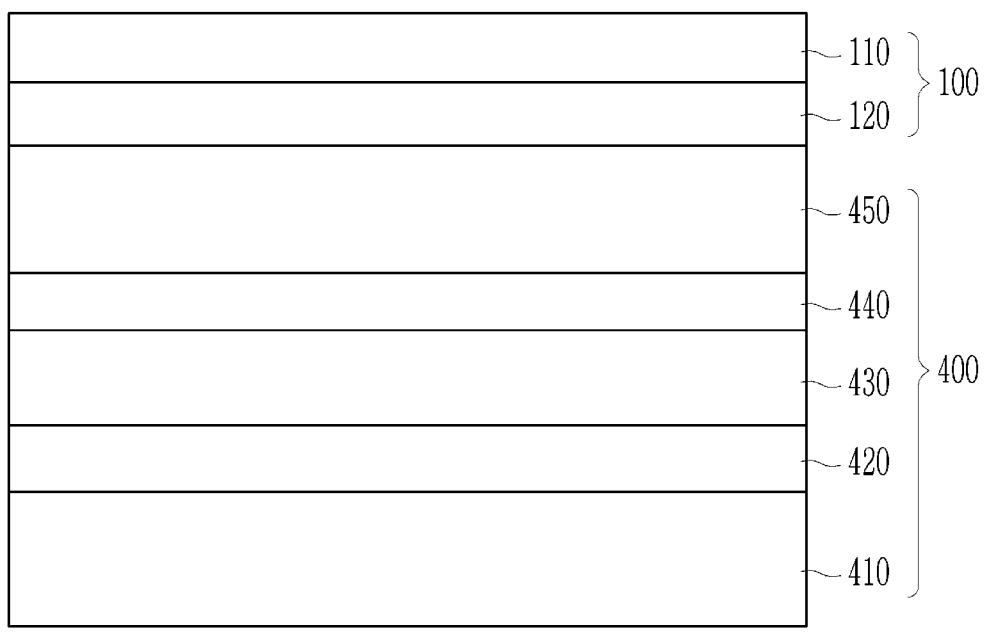
FIG. 4 is a schematic cross-sectional view of an organic light emitting diode (OLED) display, according to an embodiment.

FIG. 4 is a schematic cross-sectional view of an organic light emitting diode (OLED) display, according to an embodiment.

Referring to FIG. 4, an organic light emitting diode (OLED) display, according to an embodiment, includes an organic light emitting panel 400 and an optical film 100 disposed on one surface of the organic light emitting panel 400.

The organic light emitting panel 400 may include a base substrate 410, a lower electrode 420, an organic emission layer 430, an upper electrode 440, and an encapsulation substrate 450.

The base substrate 410 may be made of glass or a plastic.

One of the lower electrode 420 and the upper electrode 440 may be an anode and the other may be a cathode. The anode may be an electrode into which holes are injected and may be made of a transparent conductive material having a high work function and passing the emitted light externally, for example ITO or IZO. The cathode is an electrode into which electrons are injected and may be made of a conducting material having a low work function and having no effect on an organic material, for example aluminum ($A^1$), calcium (Ca), and barium (Ba).

The organic emission layer 430 includes an organic material which may emit light when applying a voltage to the lower electrode 420 and the upper electrode 440.

An auxiliary layer (not shown) may be further provided between the lower electrode 420 and the organic emission layer 430 and between the upper electrode 440 and the organic emission layer 430. The auxiliary layer may include a hole transporting layer, a hole injecting layer, an electron injecting layer, and an electron transporting layer in order to balance electrons and holes.

The encapsulation substrate 450 may be made of glass, a metal, or a polymer, and may seal the lower electrode 420, the organic emission layer 430, and the upper electrode 440 to prevent moisture and/or oxygen inflow from the outside.

The optical film 100 may be disposed at a light emitting side. For example, in the case of a bottom emission structure emitting light at the side of the base substrate 410, the optical film 100 may be disposed on the exterior side of the base substrate 710, while on the other hand, in the case of a top emission structure emitting light at the side of the encapsulation substrate 450, the optical film 100 may be disposed on the exterior side of the encapsulation substrate 450.

The optical film 100 may include the integral structured polarizer 110 and the integrally structured compensation film 120. The polarizer 110 and the compensation film 120 are the same as described above and may prevent light passing the polarizer 110 from being reflected by a metal such as an electrode of the organic light emitting panel 400 and emitting outside of the organic light emitting device, and thus, prevents visibility from being deteriorated by externally inflow light. Therefore, display characteristics of the organic light emitting diode (OLED) display may be improved.

Hereinafter, for one example of the display device, a liquid crystal display (LCD) is described.

Figure 5:
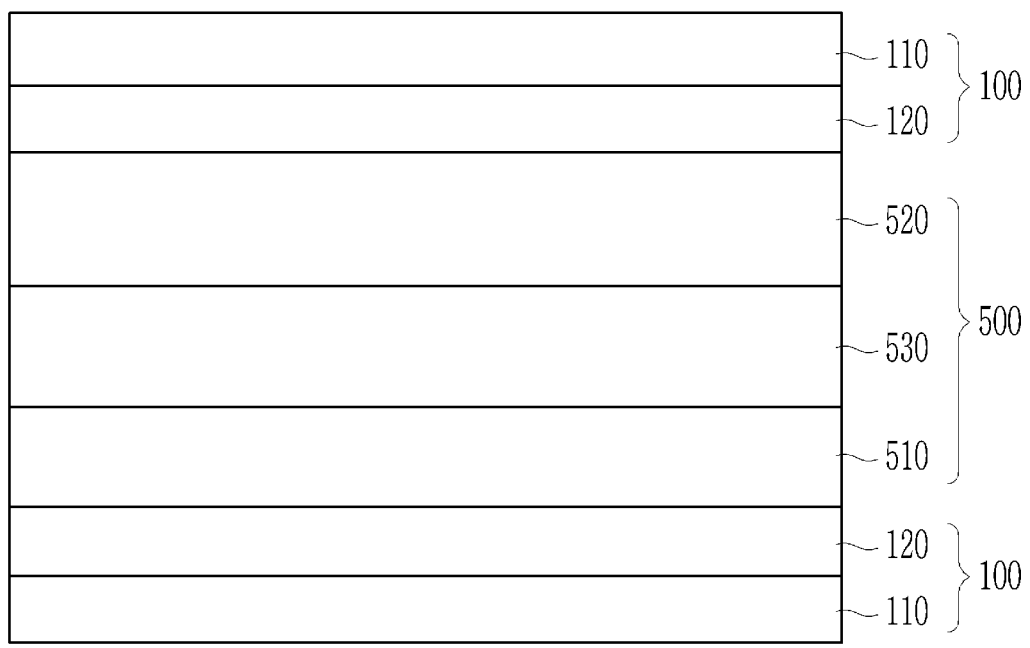
FIG. 5 is a schematic cross-sectional view of a liquid crystal display (LCD), according to an embodiment.

FIG. 5 is a schematic cross-sectional view of a liquid crystal display (LCD), according to an embodiment.

Referring to FIG. 5, a liquid crystal display (LCD), according to an embodiment, includes a liquid crystal panel 500 and an optical film 100 positioned on one surface or both surfaces of the liquid crystal panel 500.

The liquid crystal panel 500 may be a twist nematic (TN) mode panel, a vertical alignment (PVA) mode panel, an in-plane switching (IPS) mode panel, an optically compensated bend (OCB) mode panel, or the like.

The liquid crystal panel 500 may include a first display panel 510, a second display panel 520, and a liquid crystal layer 530 interposed between the first display panel 510 and the second display panel 520.

The first display panel 510 may include, for example, a thin film transistor (not shown) formed on a substrate (not shown) and a first electric field generating electrode (not shown) connected to the same, and the second display panel 520 may include, for example, a color filter (not shown) formed on a substrate (not shown) and a second electric field generating electrode (not shown). However, it is not limited thereto, and the color filter may be included in the first display panel 510, while the first electric field generating electrode and the second electric field generating electrode may be disposed on the first display panel 510 together.

The liquid crystal layer 530 may include a plurality of liquid crystal molecules. The liquid crystal molecules may have positive or negative dielectric anisotropy. In the case of the liquid crystal molecules having positive dielectric anisotropy, the major axes thereof may be aligned substantially parallel to the surface of the first display panel 510 and the second display panel 520 when not applying an electric field, and the major axes may be aligned substantially perpendicular to the surface of the first display panel 510 and second display panel 520 when applying an electric field. On the contrary, in the case of the liquid crystal molecules having negative dielectric anisotropy, the major axes may be aligned substantially perpendicular to the surface of the first display panel 510 and the second display panel 520 when not applying an electric field, and the major axes may be aligned substantially parallel to the surface of the first display panel 510 and the second display panel 520 when applying an electric field.

The optical film 100 may be disposed on the outside of the liquid crystal panel 500. Although the optical film 100 is shown to be provided on both the lower part and the upper part of the liquid crystal panel 500 in the drawing, it is not limited thereto, and it may be formed on only one of the lower part and the upper part of the liquid crystal panel 500.

Hereinafter, the present disclosure is illustrated in more detail with reference to examples. However, these examples are exemplary, and the present disclosure is not limited thereto.

EXAMPLES

Example 1: Synthesis of Compound M-1

Compound M-1 is prepared according to Reaction Scheme M-1, and a method of preparing Intermediate 1-1 and Compound M-1 as a final product are classified into Steps 1 and 2 and illustrated in detail as follows:

Reaction Scheme M-1

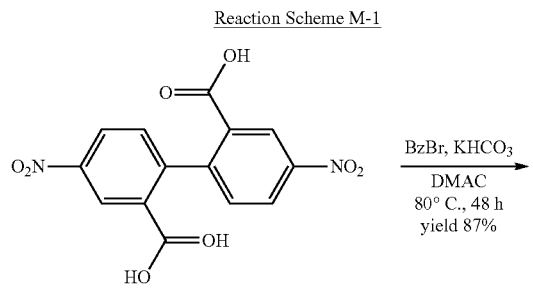

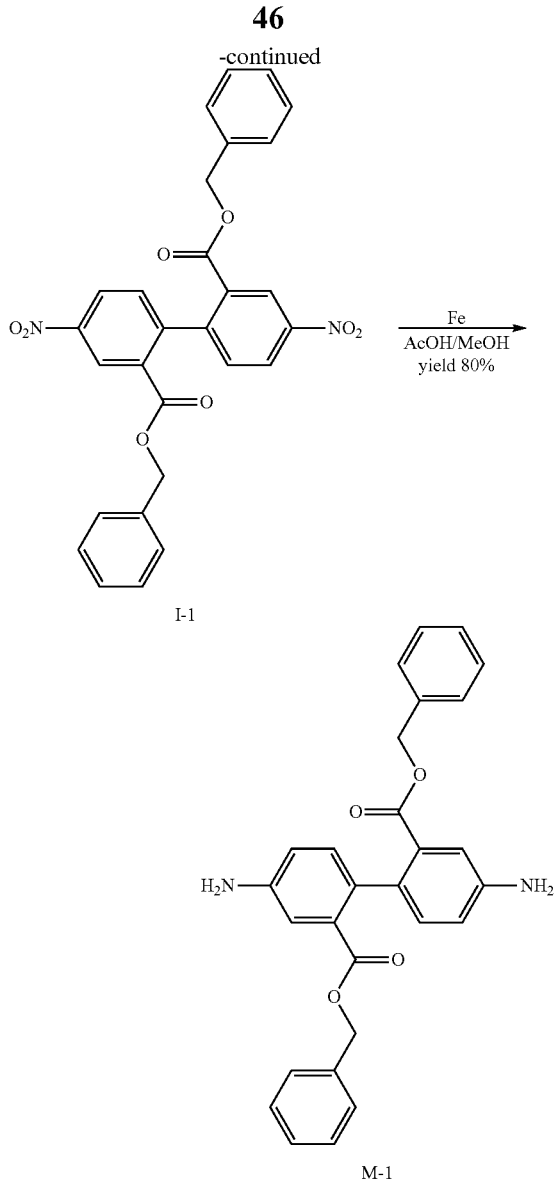

Step 1: Synthesis of Intermediate 1-1 (4,4'-dinitro-biphenyl-2,2'-dicarboxylic acid dibenzyl ester)

Figure 6:
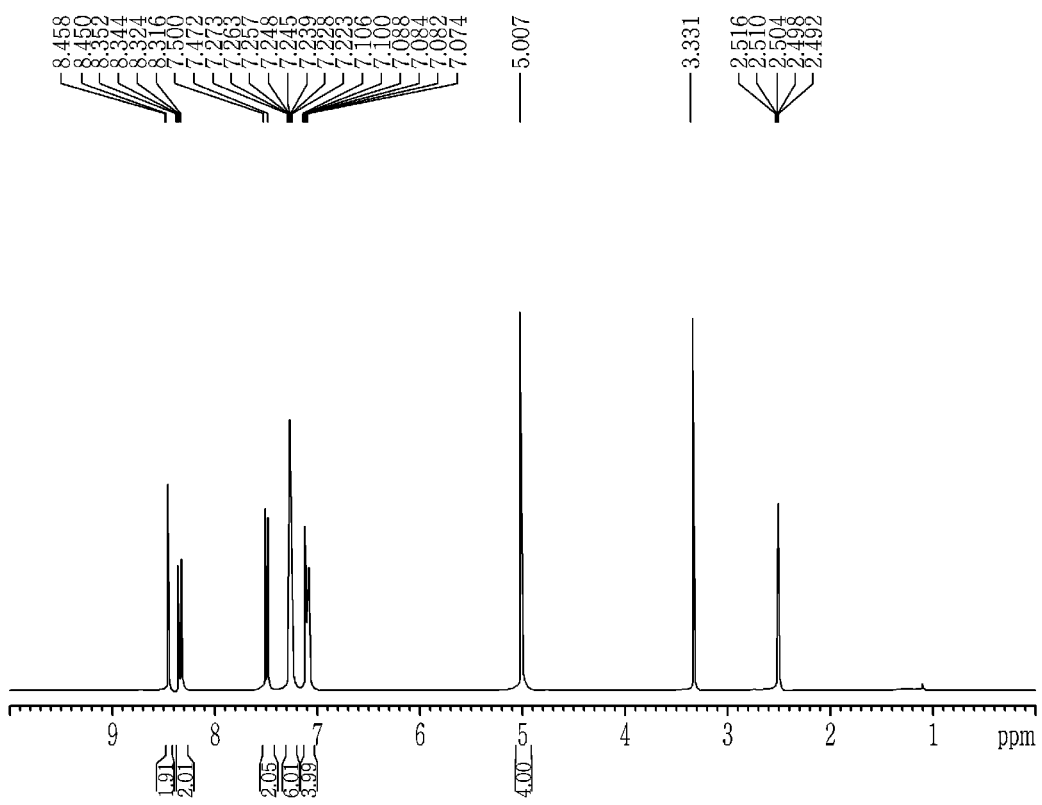
FIG. 6 is a $^1$H NMR graph of intensity versus parts per million (ppm) of an intermediate compound, 4,4'-dinitro-biphenyl-2,2'-dicarboxylic acid dibenzyl ester (Compound 1-1), formed during a preparation process of Monomer M-1 according to an exemplary embodiment.

4,4'-dinitro-2,2'-diphenic acid (mw=332.23 grams per mole (g/mol), 0.181 moles (mol), m=60 grams (gr)), benzylbromide (mw=171.04 g/mol, 0.398 mol, m=68 gr), and potassium hydrogen carbonate (m=100.12 100.12 g/mol, 0.541 mol, m=54.2 gr) are added to 0.5 liter (L) of dimethyl acetamide (DMAC), and the mixture is stirred under a nitrogen atmosphere at 80° C. for 24 hours. When a reaction is complete, the mixture is poured into 4 L of water, and surplus potassium hydrogen carbonate is decomposed by adding aqueous hydrochloric acid thereto. A brown solid precipitated therein is filtered, washed with water, and dried. A crude product is three times crystallized by using a mixed solution of dichloromethane (DCM) and methanol as a solvent. Intermediate 1-1 as a product is light yellow crystalline and has m=79.5 gr (mw=512.49 g/mol, 0.155 mol) and yield of 85.6%. A $^1$H NMR graph of Intermediate I-1 is shown in FIG. 6.

$^1$H NMR (DMSO-d$_6$) 300 MHz, δ, ppm: 5.00 (s, 4H), 7.08-7.11 (m, 4H), 7.21-7.28 (m, 6H), 7.48 (d, 2H, J$^{12}$=8.4 Hz), 8.33 (dd, 2H, J$^{12}$=8.4 Hz, J$^{13}$=2.4 Hz), 8.45 (d, 2H, J$^{13}$=2.4 Hz).

Step 2: Synthesis of Monomer M-1 (4,4'-diamino-biphenyl-2,2'-dicarboxylic acid dibenzyl esters)

Figure 7:
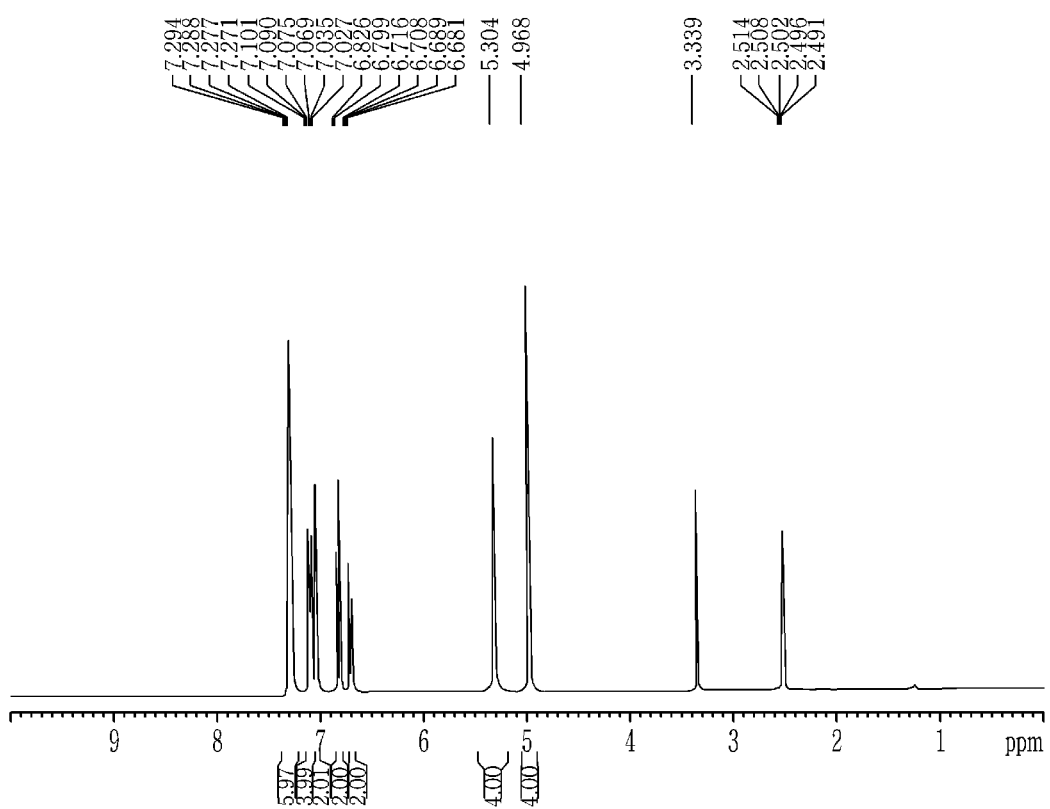
FIG. 7 is a $^1$H NMR graph of intensity versus parts per million (ppm) of Monomer M-1 (4,4'-diamino-biphenyl-2,2'-dicarboxylic acid dibenzyl ester) according to an exemplary embodiment.
Figure 8:
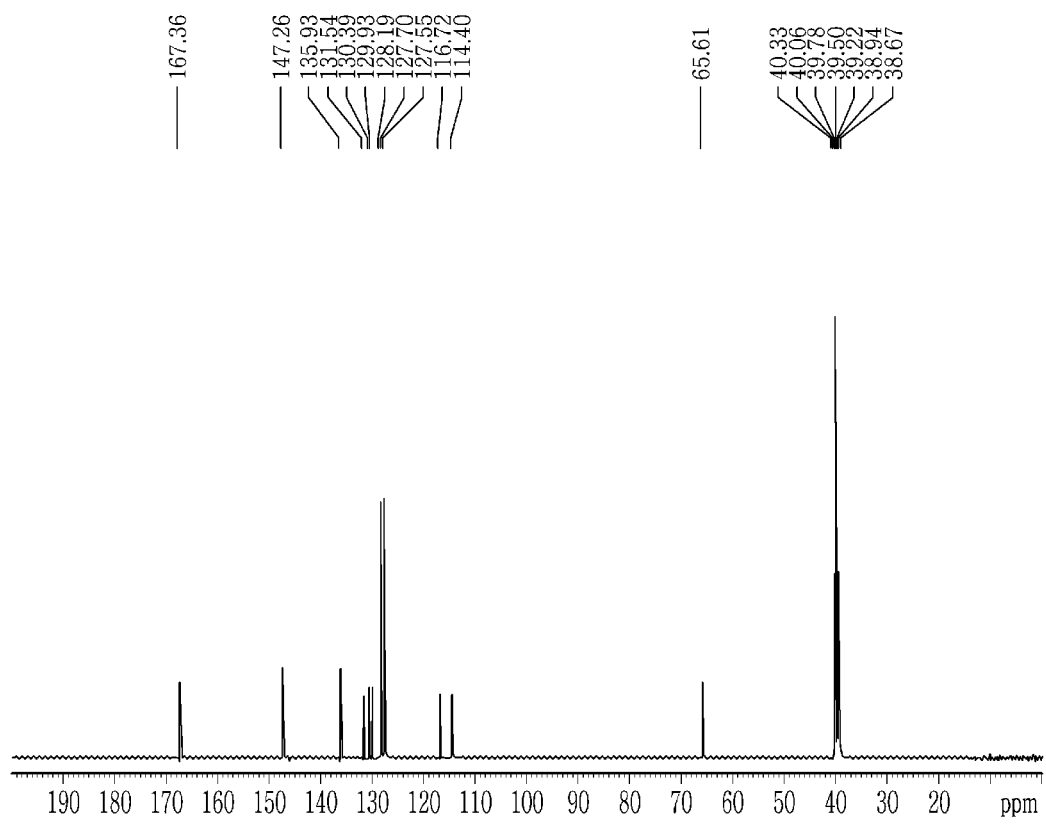
FIG. 8 is a $^{13}$C NMR graph of intensity versus parts per million (ppm) of Monomer M-1 (4,4'-diamino-biphenyl-2,2'-dicarboxylic acid dibenzyl ester) according to an exemplary embodiment.
Figure 9:
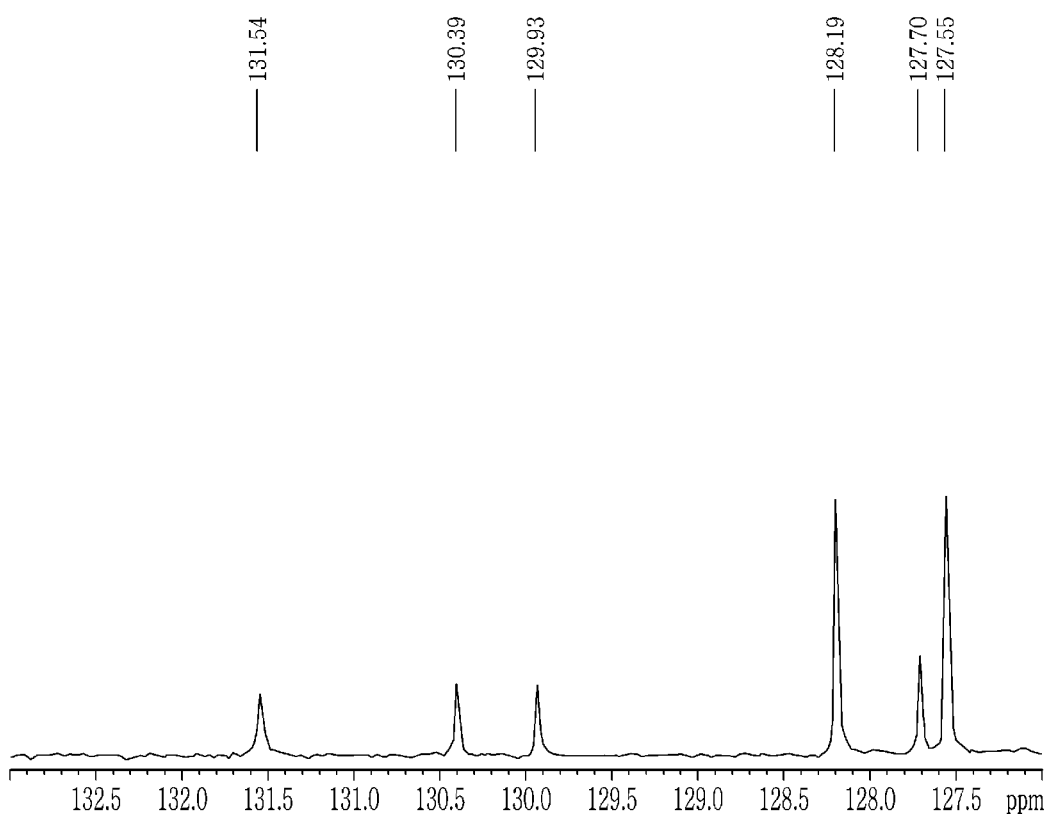
FIG. 9 is a graph of intensity versus parts per million (ppm) enlarging an aromatic area, that is, from about 127 ppm to about 133 ppm of Monomer M-1 (4,4'-diamino-biphenyl-2,2'-dicarboxylic acid dibenzyl ester) according to an exemplary embodiment of FIG. 8.
Figure 10:
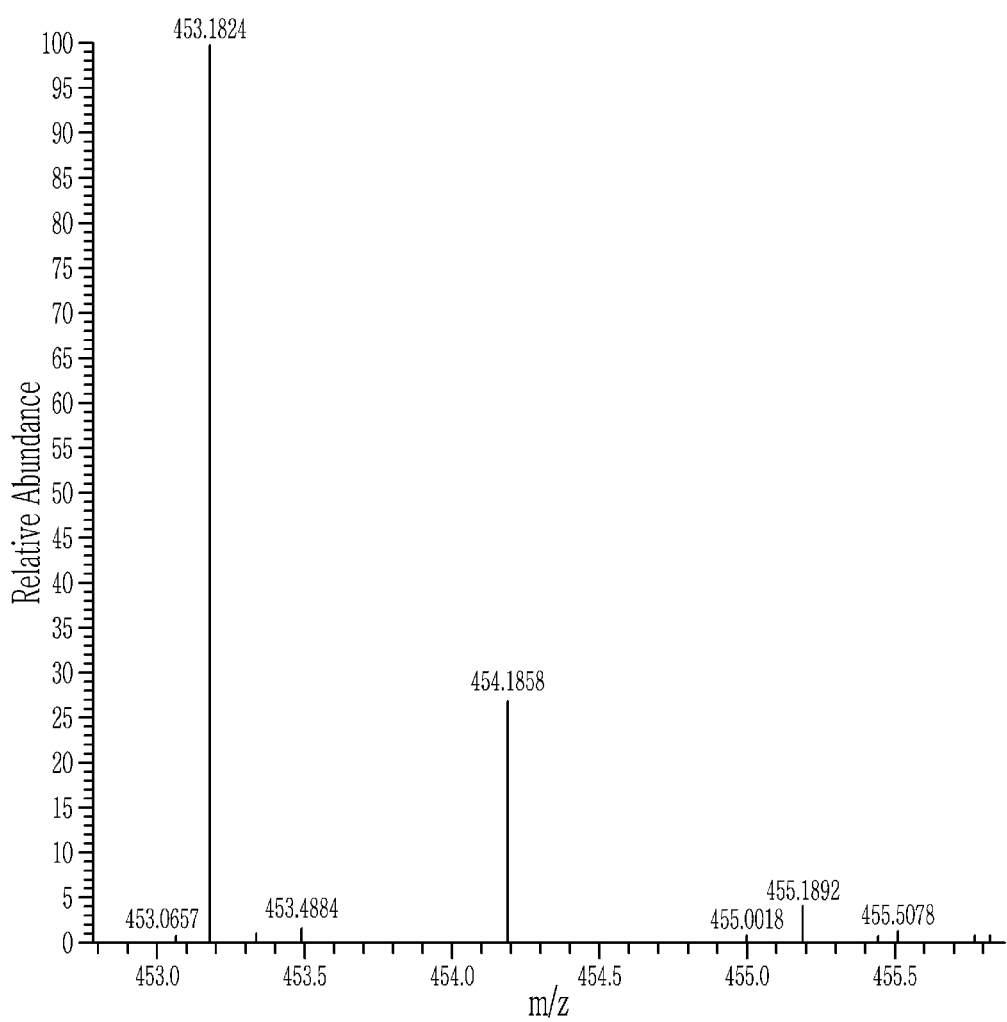
FIG. 10 is a graph of intensity versus parts per million (ppm) showing a HRMS APCI mode of Monomer M-1 (4,4'-diamino-biphenyl-2,2'-dicarboxylic acid dibenzyl ester) according to an exemplary embodiment.
Figure 11:
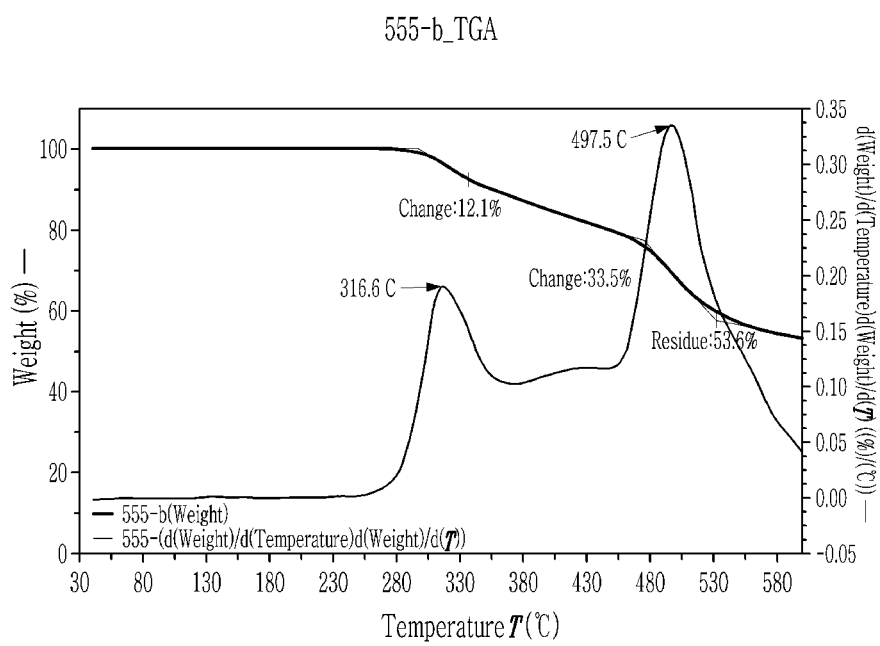
FIG. 11 is a thermogravimetric analysis (TGA) graph showing a thermal decomposition depending on a temperature of the polymer prepared from Monomer M-1 (4,4'-diamino-biphenyl-2,2'-dicarboxylic acid dibenzyl ester) according to an exemplary embodiment.
Figure 12:
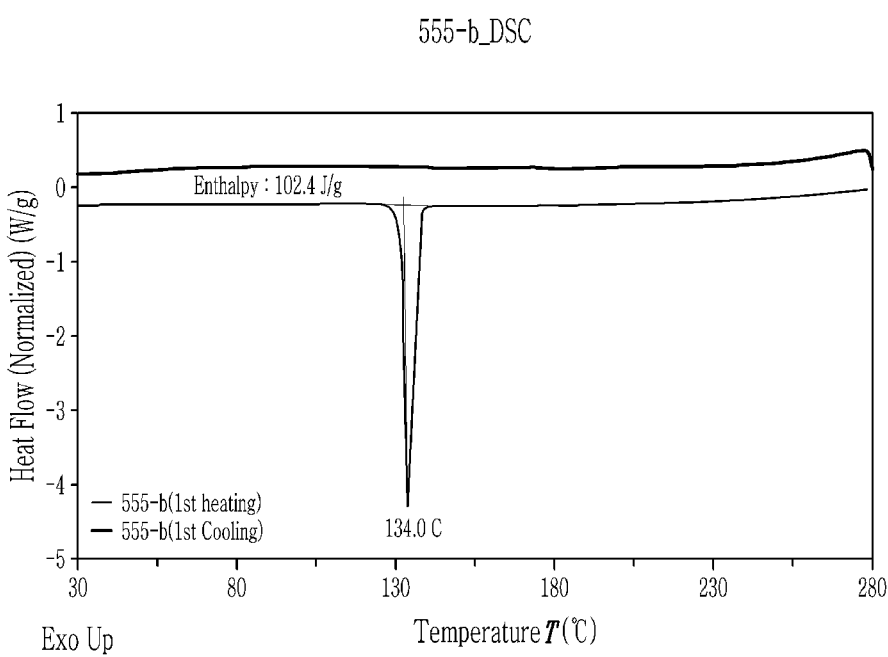
FIG. 12 is a differential scanning calorimetry (DSC) graph of the polymer prepared from Monomer M-1 (4,4'-diamino-biphenyl-2,2'-dicarboxylic acid dibenzyl ester) according to an exemplary embodiment depending on a temperature.

79.5 gr of Intermediate 1-1 (4,4'-dinitro-biphenyl-2,2'-dicarboxylic acid dibenzyl ester) (mw=512.49 g/mol, 0.155 mol) is placed into a 5 L beaker and dissolved in a mixture of 0.8 L of acetic acid and 0.2 L of methanol. 69.5 gr of iron powder (mw=55.85 g/mol, 1.24 mol) is added by small portions to the dinitro compound solution within 10 minutes while stirred. The mixture is maintained for one hour while heated and stirred (a color of a suspension gradually becomes bright). When a reaction is complete, 4 L of cold water is added to the suspension, and a diamino compound is extracted by three times using 0.5 L of ethyl acetate at each time. The collected ethyl acetate extract is washed with water (3×0.5 L) and a 5% aqueous sodium bicarbonate (2×0.5 L) and dried with magnesium sulfate. The ethyl acetate is evaporated under a reduced pressure to obtain a bright yellow solid. A crude material is dissolved in 1.5 L of water including 0.1 L of concentrated hydrochloric acid. The boiling solution is treated with two spoonful of charcoal, and filtered while hot. The filtered solution is cooled down to room temperature to precipitate white crystalline hydrochloric acid. The precipitate is filtered and then, redissolved in 1.5 L of boiling water including 50 milliliters (mL) of concentrated aqueous hydrochloric acid. The solution is once more treated with one spoonful of charcoal and filtered while hot. A resulting material is strongly stirred while a colorless hydrochloric acid solution is slowly added to 3 L of ice-cooled water including 0.3 L of 35% aqueous ammonium hydroxide. A white diamine precipitate is produced therefrom. The product is filtered, thoroughly washed with water, and dried for 12 hours in the air to remove extra water and at 80° C. under vacuum. 56 gr of Compound M-1 (mw=452.51 g/mol, 0.124 mmol) is obtained as a white solid (yield: 80%). FIG. 7 shows a $^1$H NMR graph of Compound M-1, FIG. 8 shows a $^{13}$C NMR graph, and FIG. 9 shows an enlarged aromatic ring of the $^{13}$C NMR graph. In addition, FIG. shows a HRMS APCI mode, FIG. 11 shows a TGA graph, and FIG. 12 shows a DSC graph.

$^1$H NMR (DMSO-d$_6$) 300 MHz, δ, ppm: 4.97 (s, 4H), 5.30 (s, 4H), 6.70 (dd, 2H, J$^{12}$=8.1 Hz, J$^{13}$=2.4 Hz), 6.81 (d, 2H, J$^{12}$=8.1 Hz), 7.03 (d, 2H, J$^{13}$=2.4 Hz), 7.06-7.11 (m, 4H), 7.25-7.33 (m, 6H).

$^{13}$C NMR (DMSO-d$_6$) 75 MHz, δ, ppm: 65.6, 114.4, 116.7, 127.6, 127.7, 128.2, 129.9, 130.4, 131.5, 135.9, 147.3, 167.4.

R$_f$=0.6 (blue-green fluorescent spot, EtOAc:Hex=1:1, TLC silica gel 60 F$_{254}$).

HRMS APCI (m/z): 453.1824 (measured mass), 453.1814 (calculated mass).

Thermal Analysis:
TGA (heating 10° C./min, N$_2$ atmosphere): 0.1 wt % loss 274° C., 1 wt % loss 298° C., and
DSC (heating 10° C./min, N$_2$ atmosphere): mp=134° C.

Preparation Examples 1-1 to 1-5: Preparation of Polyamic Acid and Manufacture of Film (1) Preparation of Polyamic Acid Compound M-1 according to Example 1 as a diamine, and 6FDA (4,4'-(hexafluoroisopropylidene)diphthalic anhydride), s-BPDA (3,3',4,4'-biphenyl tetracarboxylic dianhydride), and/or DA520 (ester group-containing dianhydride represented by Chemical Formula 22) as dianhydrides are mixed in each ratio shown in Table 1 and reacted to prepare each polyamic acid solution according to Preparation Examples 1-1 to 1-5.

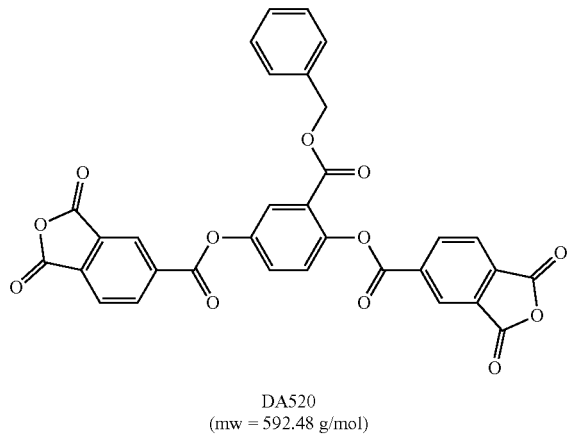

Chemical Formula 22

DA520
(mw = 592.48 g/mol)

Specifically, the polyamic acid solutions according to Preparation Examples 1-1 to 1-5 are obtained by dissolving 1 equivalent of Compound M-1 according to Example 1 as a diamine in dry DAMC, adding 1 equivalent of one kind of dianhydride or a mixture of at least two kinds of dianhydrides in each ratio shown in Table 1, and stirring the mixture at 25° C. for 36 to 48 hours.

A composition, a solid content, and polymerization time of the obtained polyamic acid solutions are shown in Table 1.

TABLE 1

| | Composition (mol %) | | | | Reaction time, hr | Solid content, wt % |
|---|---|---|---|---|---|---|
| | Dianhydride | | | Diamine | | |
| | 6-FDA | BPDA | DA520 | M-1 | | |
| Preparation Example 1-1 | 100 | — | — | 100 | 48 | 20 |
| Preparation Example 1-2 | 20 | 80 | — | 100 | 48 | 16 |
| Preparation Example 1-3 | 30 | 70 | — | 100 | 36 | 15 |
| Preparation Example 1-4 | 50 | 50 | — | 100 | 36 | 15 |
| Preparation Example 1-5 | 30 | — | 70 | 100 | 48 | 20 |

(2) Manufacture of Film

The polyamic acid solutions according to Preparation Examples 1-1 and 1-5 are respectively spin-coated at a speed of 1,500 revolutions per minute (rpm) on a 50 mm×50 mm (mm=millimeter) glass substrate, and thermally imidized to form films. Specifically, the spin coated substrates are respectively heated on a hot plate set at 80° C. for 30 minutes to be dried, and then, in a furnace, heated at a speed of 10 degrees Centigrade per minute (° C./min) from about 25° C. to about 275° C. and maintained at 275° C. for 10 minutes to form the films. Herein, the films formed by using the polyamic acid solution according to Preparation Example 1-1 are formed to have two kinds of thickness.

As for the films, thicknesses, out-of-plane birefringences ($\Delta n_{th}$), and optical characteristics such as light transmittance at 450 nanometers (nm) ($T_r$), haze, and YI are measured and shown in Table 2. Each property is measured as below:
  (i) Film Thickness: measured by using Filmetrics F20 (Filmetrics, Inc., Kanagawa, Japan)
  (ii) Out-of-plane Birefringence ($\Delta n_{th}$): measured at a wavelength of 450 nm by using a prism coupler (Metricon MODEL 2010/M)
  (iii) Optical Characteristics (Transmittance, Haze, and Yellow Index): measured by using a spectrophotometer, "Konica Minolta CM3600d" in a transmittance opacity/haze mode gence. In addition, the film according to Preparation Example 1-5 shows high transmittance of greater than or equal to 87% at 450 nm and similar haze and YI to those of the film according to Preparation Example 1-1, and thus, overall excellent optical characteristics.

Preparation Examples 1-6 to 1-10: Preparation of Polyimide and Manufacture of Film (1) Preparation of Polyimide Each polyimide solution according to Preparation Examples 1-6 to 1-10 is prepared by additionally adding 2

TABLE 2

|  | Film thickness (μm) | $\Delta n_{th}$ | Transmittance @450 nm (%) | Haze (%) | YI (%) |
|---|---|---|---|---|---|
| Preparation Example 1-1 | 8.0 | 0.0055 | 88.45 | 0.24 | 1.47 |
| Preparation Example 1-1 | 12.0 | 0.0069 | 87.17 | 0.34 | 3.72 |
| Preparation Example 1-5 | 5.0 | 0.0084 | 87.78 | 0.22 | 1.88 |

As shown in Table 2, the polyimide film formed by using novel Compound M-1 as a diamine and a known compound of 6FDA as a dianhydride according to Preparation Example 1-1 shows high transmittance of greater than or equal to 85%, specifically, greater than or equal to 87%, at 450 nm, but low haze and low YI, and thus, displays excellent optical characteristics. In addition, when the polyamic acid solution according to Preparation Example 1-1 is formed into films having a different thickness, all the films show a high out-of-plane birefringence, but in general, as the thickness is thicker, an out-of-plane birefringence is higher.

The film according to Preparation Example 1-5 is formed by using novel Compound M-1, according to an embodiment, as diamine and a mixture of novel dianhydride of the compound represented by Chemical Formula 22, DA520, along with the known compound, 6FDA, as dianhydrides, and is thinner than the film according to Preparation Example 1-1, but shows a much high out-of-plane birefrinequivalents of acetic anhydride and 2 equivalents of pyridine to each polyamic acid solution according to Preparation Examples 1-1 to 1-5 and stirring the mixture at 25° C. for 2 to 12 hours for a partially chemical imidization. Compositions, imidization times, solid contents, and inherent viscosity (Winn) of the obtained polyimide solutions are shown in Table 3.

The inherent viscosity (Winn) is measured regarding 0.5 grams per deciliter (g/dL) of a polymer solution in DMAc by using Cannon PolyVisc Automated Viscosimeter.

TABLE 3

|  | Composition, mol % | | | | Imidization time, hr | Solid content, wt % | $\eta_{inh}$, dL/g |
|---|---|---|---|---|---|---|---|
|  | Dianhydride | | | Diamine | | | |
|  | 6-FDA | BPDA | DA520 | M-1 | | | |
| Preparation Example 1-6 | 100 | — | — | 100 | 12 | 15 | 1.00 |
| Preparation Example 1-7 | 20 | 80 | — | 100 | 12 | 11 | gel |
| Preparation Example 1-8 | 30 | 70 | — | 100 | 2 | 10 | 1.22 |
| Preparation Example 1-9 | 50 | 50 | — | 100 | 2 | 10 | 1.48 |
| Preparation Example 1-10 | 30 | — | 70 | 100 | 12 | 15 | 1.38 |

(2) Manufacture of Film

The polyimide solutions according to Preparation Examples 1-6, 1-8, 1-9, and 1-10 are respectively spin-coated at a speed of 200 rpm to 3,000 rpm on a 50×50 mm glass substrate. The coated film is dried on a hot plate set at 80° C. for 30 minutes and heated at a temperature-increasing rate of 10° C./min from about 25° C. to about 225° C., and then, maintained at 225° C. for 20 minutes in a furnace. Herein, the polyimide films according to Preparation Examples 1-6 and 1-10 are respectively formed to have various thicknesses. A thickness, an out-of-plane birefringence ($\Delta n_{th}$), light transmittance (%) at 450 nm, haze, YI, and a glass transition temperature of the film are measured and shown in Table 4.

The glass transition temperature (T g) is measured by using a thermal mechanical analyzer (TMA Q400, TA Instruments) with a fixed tension force of 0.05 Newtons (N) at a speed of 5° C./min within a temperature range of 50° C. to 400° C.

TABLE 4

| | Film thickness, μm | $\Delta n_{th}$ | Tr at 450 nm, % | Haze, % | YI, % | $T_g$, °C. |
|---|---|---|---|---|---|---|
| Preparation Example 1-6 | 4.0 | 0.0185 | 88.73 | 0.27 | 1.06 | — |
| | 9.0 | 0.0191 | 88.42 | 0.3 | 1.53 | — |
| | 11.0 | 0.0150 | 89.36 | 0.33 | 1.43 | 201 |
| | 13.0 | 0.0118 | 88.24 | 0.31 | 1.79 | — |
| Preparation Example 1-8 | 14.0 | 0.0104 | 86.04 | 0.52 | 4.48 | — |
| Preparation Example 1-9 | 9.0 | 0.0102 | 87.03 | 0.61 | 3.02 | — |
| Preparation Example 1-10 | 10.0 | 0.0175 | 87.74 | 0.29 | 1.94 | — |
| | 14.0 | 0.0242 | 86.93 | 0.4 | 3.14 | — |
| | 17.0 | 0.0245 | 86.56 | 0.44 | 3.7 | — |

As shown in Tables 3 and 4, polyimide films may have a different out-of-plane birefringence depending on a method of forming the polyimide films, which are formed by using a polyamic acid solution having the same composition through a thermal imidization or chemical imidization. However, a polyimide film formed by using a novel diamine compound M-1, according to an embodiment, has excellent optical properties such as high light transmittance at 450 nm, low haze, and low YI despite an overall thin thickness, for example, a thickness of less than 20 μm and also, shows a high out-of-plane birefringence, and thus, may be suitably used as an optical film, for example, a compensation film regardless of a thermal or chemical imidization.

As shown in Table 2, as a film thickness is thicker, an out-of-plane birefringence tends to be larger, and transmittance at 450 nm, haze, YI, and the like are not substantially much deteriorated.

In addition, the film obtained by mixing novel dianhydride, DA520, with known dianhydride, 6FDA, and reacting them with novel diamine, Compound M-1, according to Preparation Example 1-10, has a much higher out-of-plane birefringence at an equivalent or similar thickness, and in addition, maintains excellent properties, such as, light transmittance at 450 nm, haze, YI, and the like compared with the films formed by using known dianhydride, 6FDA alone (Preparation Example 1-6) or mixing another known dianhydride, s-BPDA, along with 6FDA (Preparation Examples 1-8 and 1-9).

Preparation Examples 1-11 and 1-16: Preparation of Poly(amide-imide) and Manufacture of Film (1) Preparation of Poly(amide-imide)

Each poly(amide-imide) copolymer according to Preparation Examples 1-11 to 1-16 is prepared by mixing Compound M-1 according to Example 1, 6FDA as a dianhydride, and TPCI (terephthaloyl chloride) or BPCI (biphenyl dicarbonylchloride) as a dicarboxylic acid derivative in a ratio shown in Table 5 and reacting them.

Specifically, 2 equivalents of Compound M-1 according to Example 1 as a diamine and 1 equivalent of 6-FDA as a dianhydride are added to DAMC and reacted therewith at 25° C. for 24 to 48 hours to obtain an amic acid solution capped with an amino group at both ends. Subsequently, 1 equivalent of a dicarboxylic acid derivative, TPCI or BPCI, are added to the obtained amic acid solution in a ratio shown in Table 2, reacted and copolymerized at 25° C. for 2 hours, added with 2 equivalents of acetic anhydride and 2 equivalents of pyridine, and further reacted at 25° C. for 2 to 14 hours to obtain a chemically partially imidized poly(amide-imide) copolymer solutions according to Preparation Examples 1-11 to 1-16.

A composition, reaction time, a solid content, and inherent viscosity ($\eta_{inh}$) of the obtained poly(amide-imide) copolymers are shown in Table 5.

TABLE 5

| | Composition (mol %) | | | | Polymerization reaction time (hr) | Imidization time (hr) | Solid content (wt %) | $\eta_{inh}$, dL/g |
|---|---|---|---|---|---|---|---|---|
| | 6-FDA | TPCI | BPCI | M-1 | | | | |
| Preparation Example1-11 | 50 | 50 | | 100 | 50 | 2 | 8 | 1.56 |
| Preparation Example1-12 | 50 | | 50 | 100 | 50 | 2 | 8 | 0.89 |
| Preparation Example1-13 | 80 | 20 | | 100 | 26 | 14 | 12 | — |
| Preparation Example1-14 | 60 | 40 | | 100 | 26 | 14 | 11 | — |
| Preparation Example1-15 | 40 | 60 | | 100 | 26 | 14 | 11 | — |
| Preparation Example1-16 | 20 | 80 | | 100 | 26 | 14 | 7 | — |

(2) Manufacture of Film

The poly(amide-imide) copolymer films according to Preparation Examples 1-11 to 1-16 are formed by using the same chemical imidization as illustrated in Preparation Examples 1-6 to 1-10, except for using the poly(amide-imide) solutions according to Preparation Examples 1-11 to 1-16 instead of the polyimide solutions according to Preparation Examples 1-6 to 1-10, and then, a thickness, an out-of-plane birefringence ($\Delta n_{th}$), light transmittance (%) at 450 nm, haze, YI, and $T_g$ of the films are measured and shown in Table 6. Each property is measured by the same method as above.

TABLE 6

| | Film thickness (μm) | $\Delta n_{th}$ | Tr at 450 nm (%) | Haze (%) | YI (%) | $T_g$ (° C.) |
|---|---|---|---|---|---|---|
| Preparation Example 1-11 | 6.0 | 0.0620 | 88.77 | 0.42 | 0.91 | 295 |
| Preparation Example 1-12 | 2.0 | 0.0740 | 88.49 | 1.15 | 0.82 | — |
| Preparation Example 1-13 | 8.4 | 0.0075 | 89.47 | 0.28 | 0.93 | 198 |
| Preparation Example 1-14 | 8.7 | 0.0182 | 89.36 | 0.15 | 0.82 | 198 |
| Preparation Example 1-15 | 11.0 | 0.0534 | 88.81 | 0.33 | 1.01 | 196 |
| Preparation Example 1-16 | 7.3 | 0.1002 | 88.11 | 0.24 | 0.91 | 214 |

As shown in Table 6, a poly(amide-imide) copolymer film formed by using Compound M-1 as a novel diamine compound, according to an embodiment, 6FDA as a known dianhydride, and a known aromatic dicarboxylic acid derivative has a very thin thickness of around 10 μm but a very high out-of-plane birefringence ($\Delta n_{th}$). In addition, the film has very high light transmittance of greater than or equal to 88% at 450 nm and excellent optical characteristics, such as, haze, YI, and the like. In addition, the film has a glass transition temperature of greater than or equal to 190° C., and thus, high heat resistance and excellent mechanical characteristics.

Comparative Preparation Examples 1-1 and 1-2: Preparation of Poly(amide-imide) and Manufacture of Film

(1) Preparation of Poly(amide-imide)

Poly(amide-amic acid) is prepared by using TFDB (2,2'-bis(trifluoromethyl)benzidine), instead of Compound M-1 according to Example 1 as diamine.

Specifically, polyamic acid caped with an amino group at both ends is obtained by adding 2 equivalents of TFDB as diamine and 1 equivalent of 6-FDA as a dianhydride to DMAc and reacting them at 25° C. for 24 hours. Then, chemically partially imidized poly(amide-imide) copolymer solutions according to Comparative Preparation Examples 1-1 and 1-2 are obtained by respectively adding 1 equivalent of a dicarboxylic acid derivative, TPCI or BPCI, to the obtained polyamic acid solution as shown in Table 6, copolymerizing the mixture at 25° C. for 1 hour, adding 2 equivalent of acetic anhydride and 2 equivalent of pyridine thereto, and further reacting them at 25° C. for 2 hours.

A composition, a solid content, and inherent viscosity (Winn) of the obtained poly(amide-imide) copolymer solution are shown in Table 7.

TABLE 7

| | Composition, mol % | | | | Solid content, wt % | $\eta_{inh}$, dL/g |
|---|---|---|---|---|---|---|
| | Dianhydride | Dichloroanhydride | | Diamine | | |
| | 6-FDA | TPCI | BPCI | TFDB | | |
| Comparative Preparation Example 1-1 | 50 | 50 | | 100 | 15 | 0.69 |
| Comparative Preparation Example 1-2 | 50 | | 50 | 100 | 11 | 1.46 |

As shown in Table 7, the films according to Comparative Preparation Examples 1-1 and 1-2 have the same composition as those of the poly(amide-imide) copolymer film according to Preparation Examples 1-11 and 1-12, except for using a known compound, TFDB, instead of Compound M-1 according to Example 1 as diamine.

(2) Manufacture of Film

A poly(amide-imide) copolymer film is formed by using the same chemical imidization as illustrated in Preparation Examples 1-6 to 1-10, except for using the poly(amide-imide) copolymer solutions according to Comparative Preparation Examples 1-1 and 1-2 instead of the polyimide solutions according to Preparation Examples 1-6 to 1-10, and then, a thickness, an out-of-plane birefringence ($\Delta n_{th}$), light transmittance (%) at 450 nm, haze, and YI of the film are measured and shown in Table 8. Each property is measured as illustrated above.

TABLE 8

| | Film thickness (μm) | $\Delta n_{th}$ | Transmittance@ 450 nm (%) | Haze (%) | YI (%) |
|---|---|---|---|---|---|
| Comparative Preparation Example 1-1 | 9.0 | 0.0540 | 90.57 | 0.15 | 0.42 |
| Comparative Preparation Example 1-2 | 18.0 | 0.0460 | 89.70 | 0.21 | 0.90 |

As shown in Table 8, the poly(amide-imide) copolymer films formed to have the same composition as those of Preparation Examples 1-11 and 1-12 by using known TFDB instead of Compound M-1, according to Example 1, as a diamine, according to Comparative Preparation Examples 1-1 and 1-2, have a much thicker thickness, but a lower out-of-plane birefringence ($\Delta n_{th}$) than those of the films according to Preparation Examples 1-11 and 1-12. The films may have a little higher or equivalent optical characteristics such as light transmittance at 450 nm, haze, and YI compared with those of the films according to Preparation Examples 1-11 and 1-12.

SUMMARY

As illustrated hereinbefore, the film including a polyimide prepared by polymerizing the novel diamine Compound M-1, according to Example 1, with a dianhydride or a poly(amide-imide) copolymer prepared by polymerizing the novel diamine Compound M-1 according to Example 1, a dianhydride, and a dicarboxylic acid derivative has excellent optical characteristics such as high light transmittance of greater than or equal to 85%, for example, greater than or equal to 86%, for example, greater than or equal to 87%, for example, greater than or equal to 88% at 450 nm, low haze, and low YI, particularly, a thin film thickness, for example, a thickness of less than or equal to 100 μm, for example, less than or equal to 80 μm, for example, less than or equal to 50 μm, for example, less than or equal to 30 μm, for example, less than or equal to 20 μm, and a high out-of-plane birefringence ($\Delta n_{th}$) compared with a polyimide or poly (amide-imide) film formed by using a known diamine, and thus, may be usefully used as an optical film, for example, a compensation film and the like.

Furthermore, the novel compounds, according to an embodiment, may be easily prepared from an inexpensive starting material, and thus, have an effect of sharply reducing a manufacturing cost when replaced with an expensive conventional aromatic diamine and/or aromatic dianhydride to prepare a film having high optical properties and high mechanical properties.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A polymer being a product of reactants comprising a dianhydride and a monomer represented by Chemical Formula 1:

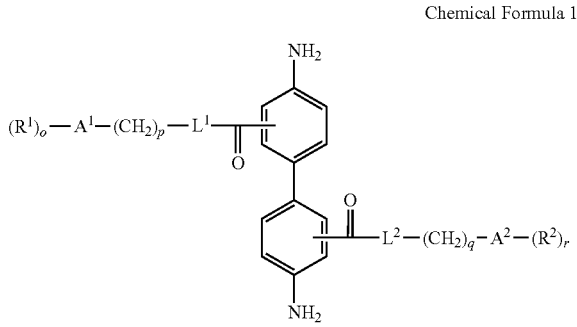

Chemical Formula 1 wherein, in Chemical Formula 1,
$L^1$ and $L^2$ are O,
$A^1$ and $A^2$ are independently a benzene ring or a C3 to C30 hetero aromatic ring,
p and q are independently an integer ranging from 1 to 20,
o and r are independently an integer ranging from 0 to 3, and
$R^1$ and $R^2$ are independently hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C2 to C30 heteroaryl group, a substituted or unsubstituted C7 to C30 arylalkyl group, a hydroxy group, a halogen, a nitro group, —NR'R'', —CO—NR'R'', —SiR'R''R''' (wherein R', R'', and R''' are independently hydrogen, a C1 to C30 alkyl group, a C6 to C30 aryl group, or a C7 to C30 arylalkyl group), or a group represented by Chemical Formula 2:

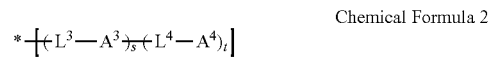

Chemical Formula 2 wherein, in Chemical Formula 2,
$L^3$ and $L^4$ are independently O, CO, COO, C≡C, or CONR$^b$ (wherein, R$^b$ is hydrogen or a C1 to C30 alkyl group),
$A^3$ and $A^4$ are independently a substituted or unsubstituted C6 to C30 aromatic ring, a substituted or unsubstituted fluorene ring, a substituted or unsubstituted C7 to C30 arylalkyl group, or a substituted or unsubstituted C3 to C30 hetero aromatic ring group, and
s and t are independently an integer ranging from 0 to 3.

2. The polymer of claim 1, wherein
$A^1$ and $A^2$ are independently a benzene ring, or a C3 to C20 hetero aromatic ring with at least one carbon is replaced by at least one of nitrogen or sulfur,
p and q are independently an integer ranging from 1 to 6,
o and r are independently an integer ranging from 0 to 2, and
$R^1$ and $R^2$ are independently hydrogen, a C1 to C20 alkyl group, a C1 to C10 alkoxy group, a C6 to C20 aryl group, a C2 to C20 heteroaryl group, a C7 to C20 arylalkyl group, a halogen, a nitro group, —CO—NR'R'' (wherein, R' and R'' are independently hydrogen, a C1 to C30 alkyl group, a C6 to C30 aryl group, or a C7 to C30 arylalkyl group), or a group represented by Chemical Formula 2:

Chemical Formula 2 wherein, in Chemical Formula 2,
$L^3$ and $L^4$ are independently O, CO, COO, C≡C, or CONH,
$A^3$ and $A^4$ are independently a substituted or unsubstituted C6 to C20 aromatic ring group, or a substituted or unsubstituted C3 to C20 heteroaromatic ring group wherein at least one carbon is replaced by at least one of nitrogen and sulfur, and
s and t are independently an integer ranging from 0 to 2, provided that 1≤s+t≤2.

3. The polymer of claim 1, wherein
$A^1$ and $A^2$ are independently selected from benzene, pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine,
p and q are independently 1 or 2,
o and r are independently 0 or 1, and
$R^1$ and $R^2$ are independently hydrogen, a C1 to C10 alkyl group, a C1 to C10 alkoxy group, a C6 to C10 aryl group, a halogen, a nitro group, —CO—NR'R''

(wherein, R' and R" are independently hydrogen, a C1 to C20 alkyl group, a C6 to C20 aryl group, or a C7 to C20 arylalkyl group), or a group represented by Chemical Formula 2:

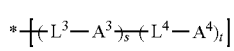

Chemical Formula 2 wherein, in Chemical Formula 2,
$L^3$ and $L^4$ are independently COO, C≡C, or CONH,
$A^3$ and $A^4$ are a substituted or unsubstituted benzene ring, and
s and t are independently an integer ranging from 0 to 2, provided that 1≤s+t≤2.

4. The polymer of claim 1, wherein the monomer represented by Chemical Formula 1 is represented by Chemical Formula 3:

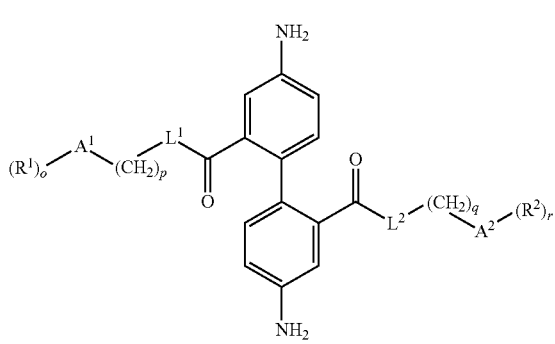

Chemical Formula 3 wherein, in Chemical Formula 3,
$L^1$, $L^2$, $A^1$, $A^2$, $R^1$, $R^2$, o, p, q, and r are the same as defined in Chemical Formula 1.

5. The polymer of claim 4, wherein in Chemical Formula 3,
$A^1$ and $A^2$ are independently a benzene ring, or a C3 to C20 hetero aromatic ring with at least one carbon is replaced by at least one of nitrogen of sulfur,
p and q are independently an integer ranging from 1 to 6,
o and r are independently an integer ranging from 0 to 2, and
$R^1$ and $R^2$ are independently a C1 to C10 alkyl group, a C6 to C10 aryl group, a C1 to C10 alkoxy group, a hydroxyl group, a halogen, or a group represented by Chemical Formula 2:

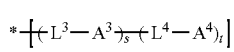

Chemical Formula 2 wherein, in Chemical Formula 2,
$L^3$ and $L^4$ are independently O, CO, COO, C≡C, or CONH,
$A^3$ and $A^4$ are independently a substituted or unsubstituted C6 to C20 aryl group or a substituted or unsubstituted C3 to C20 heteroaryl group wherein at least one carbon is replaced by at least one of nitrogen and sulfur, and
s and t are independently an integer ranging from 0 to 2, provided that 1≤s+t≤2.

6. The polymer of claim 4, wherein in Chemical Formula 3,
$A^1$ and $A^2$ are independently selected from benzene, pyrazole, imidazole, thiazole, triazole, pyridine, pyridazine, pyrimidine, pyrazine, triazine, indazole, indolizine, benzimidazole, benzothiazole, benzothiophene, benzopurine, isoquinoline, or purine,
p and q are independently 1 or 2,
o and r are independently 0 or 1, and
$R^1$ and $R^2$ are independently hydrogen, a C1 to C10 alkyl group, a C1 to C10 alkoxy group, a C6 to C10 aryl group, a halogen, a nitro group, —CO—NR'R" (wherein, R' and R" are independently hydrogen, a C1 to C20 alkyl group, a C6 to C20 aryl group, or a C7 to C20 arylalkyl group), or a group represented by Chemical Formula 2:

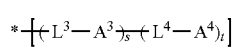

Chemical Formula 2 wherein, in Chemical Formula 2,
$L^3$ and $L^4$ are independently COO, C≡C, or CONH,
$A^3$ and $A^4$ are a substituted or unsubstituted benzene ring, and
s and t are independently an integer ranging from 0 to 2, provided that 1≤s+t≤2.

7. The of claim 4, wherein in Chemical Formula 3,
$A^1$ and $A^2$ are independently selected from benzene or benzothiazole,
p and q are independently 1 or 2,
o and r are independently 0 or 1, and
$R^1$ and $R^2$ are independently hydrogen, an iso-propyl group, a t-butyl group, a fluorine group, a nitro group, a methoxy group, an ethoxy group, —CO—NR'R" (wherein, R' and R" are independently hydrogen, a C1 to C10 alkyl group, or a C6 to C10 aryl group), or a group represented by Chemical Formula 2:

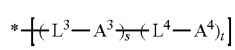

Chemical Formula 2 wherein in Chemical Formula 2,
$L^3$ and $L^4$ are independently COO, C≡C, or CONH,
$A^3$ and $A^4$ are a substituted or unsubstituted benzene ring, and
s and t are independently an integer ranging from 0 to 2, provided that 1≤s+t≤2.

8. The polymer of claim 1, wherein the dianhydride is represented by Chemical Formula 4-1 or Chemical Formula 4-2:

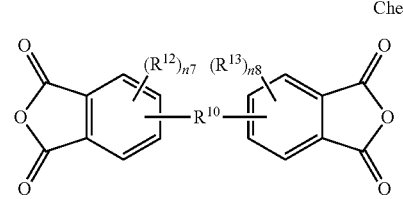

Chemical Formula 4-1 wherein in Chemical Formula 4-1, $R^{10}$ is a single bond, —O—, —S—, —C(=O)—, —CH(OH)—, —C(=O)NH—, —S(=O)$_2$—, —Si(CH$_3$)$_2$—, —(CH$_2$)$_p$—, —(CF$_2$)$_q$—, —C(C$_n$H$_{2n+1}$)$_2$—, —C(C$_n$F$_{2n+1}$)$_2$—, —(CH$_2$)$_p$—C(C$_n$H$_{2n+1}$)$_2$—(CH$_2$)$_q$—, or —(CH$_2$)$_p$—C(C$_n$F$_{2n+1}$)$_2$—(CH$_2$)$_q$— (wherein 1≤n≤10, 1≤p≤10, and 1≤q≤10), $R^{12}$ and $R^{13}$ are independently a halogen, a hydroxy group, a substituted or unsubstituted C1 to C10 aliphatic organic group, a substituted or unsubstituted C6 to C20 aromatic organic group, a —OR$^{201}$ group (wherein R$^{201}$ is a C1 to C10 aliphatic organic group), or a —SiR$^{210}$R$^{211}$R$^{212}$ (wherein R$^{210}$, R$^{211}$, and R$^{212}$ are independently hydrogen or a C1 to C10 aliphatic organic group) group, and n7 and n8 are independently one of integers of 0 to 3;

Chemical Formula 4-2

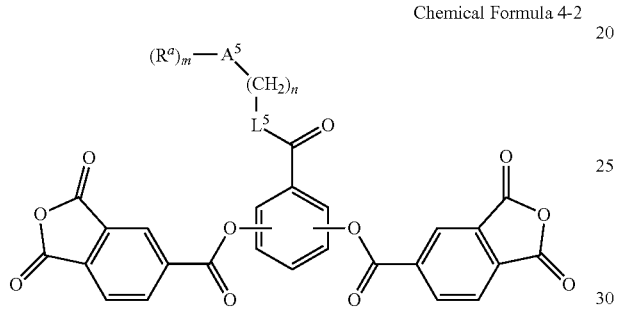

wherein, in Chemical Formula 4-2, $L^5$ is 0 or NR$^b$ (wherein, R$^b$ is hydrogen or a C1 to C20 alkyl group), $A^5$ is a C6 to C30 aromatic organic group, and $R^a$ is hydrogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C6 to C30 aryl group, a substituted or unsubstituted C7 to C30 arylalkyl group, a hydroxy group, a halogen, a nitro group, —NR'R", —CO—NR'R", —SiR'R"R'" (wherein R', R", and R'" are independently hydrogen, a C1 to C30 alkyl group, a C6 to C30 aryl group, or a C7 to C30 arylalkyl group), or a group represented by Chemical Formula A:

Chemical Formula A

wherein, in Chemical Formula A, $L^3$ and $L^4$ are independently O, CO, COO, C≡C, or CONR$^b$ (wherein, R$^b$ is hydrogen or a C1 to C30 alkyl group), $A^3$ and $A^4$ are independently a substituted or unsubstituted C6 to C30 aromatic ring, a substituted or unsubstituted fluorene ring, or a substituted or unsubstituted C7 to C30 arylalkyl group, s and t are independently an integer ranging from 0 to 3, m of Chemical Formula 4-2 is an integer ranging from 0 to 3, and n is an integer ranging from 0 to 20.

9. The polymer of claim 8, wherein the dianhydride represented by Chemical Formula 4-1 comprises a dianhydride represented by Chemical Formula 5-1, a dianhydride represented by Chemical Formula 6-1, or a combination thereof, and the dianhydride represented by Chemical Formula 4-2 comprises a dianhydride represented by Chemical Formula 5-2, a dianhydride represented by Chemical Formula 6-2, or a combination thereof:

Chemical Formula 5-1

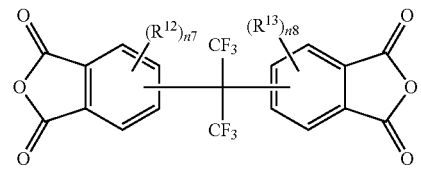

Chemical Formula 6-1

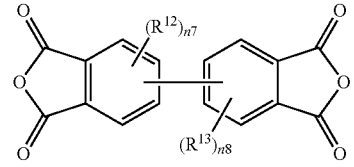

wherein, in Chemical Formula 5-1 and Chemical Formula 6-1, $R^{12}$ and $R^{13}$ are the same or different and are independently a halogen, a hydroxy group, an alkoxy group (—OR$^{208}$, wherein R$^{208}$ is a C1 to C10 aliphatic organic group), a silyl group (—SiR$^{209}$R$^{210}$R$^{211}$, wherein R$^{209}$, R$^{210}$, and R$^{211}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n7 and n8 are independently an integer ranging from 0 to 3;

Chemical Formula 5-2

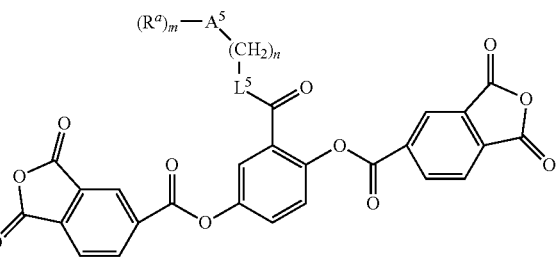

Chemical Formula 6-2

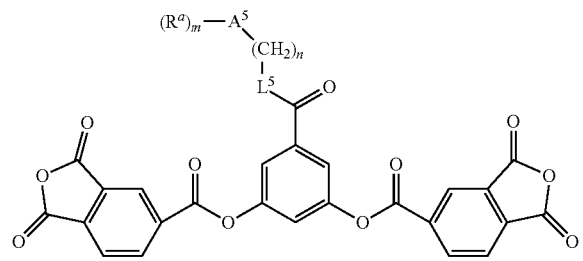

wherein, in Chemical Formula 5-2 and Chemical Formula 6-2, $L^5$, $A^5$, $R^a$, m, and n are the same as defined in Chemical Formula 4-2.

10. The polymer of claim 1, wherein the reactants further comprising a dicarboxylic acid derivative represented by Chemical Formula 7:

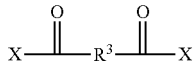

Chemical Formula 7 wherein, in Chemical Formula 7,
$R^3$ is at least one of a substituted or unsubstituted phenylene group and a substituted or unsubstituted biphenylene group, and each of X is the same or different and is a halogen atom.

11. The polymer of claim 10, wherein $R^3$ of Chemical Formula 7 is at least one of an unsubstituted phenylene group and an unsubstituted biphenylene group, and each of X is independently Cl or Br.

12. The polymer of claim 1, wherein the reactants further comprising diamine represented by Chemical Formula 8:

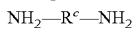

Chemical Formula 8 wherein, in Chemical Formula 8,
$R^c$ is a substituted or unsubstituted C6 to C30 aromatic organic group, wherein the substituted or unsubstituted C6 to C30 aromatic organic group is present as a substituted or unsubstituted single aromatic ring; a fused ring comprising two or more substituted or unsubstituted aromatic rings; or a ring system comprising two or more of the substituted or unsubstituted single aromatic ring and/or the fused ring that are linked by a single bond, or a functional group of a fluorenylene group, a substituted or unsubstituted C1 to C10 cycloalkylene group, a substituted or unsubstituted C6 to C15 arylene group, —O—, —S—, —C(=O)—, —CH(OH)—, —S(=O)$_2$—, —Si(CH$_3$)$_2$—, —(CH$_2$)$_p$— (wherein, 1≤p≤10), —(CF$_2$)$_q$—, wherein, 1≤q≤10), —C(CH$_3$)$_2$—, —C(CF$_3$)$_2$—, —C(=O)NH—, or a combination thereof.

13. The polymer of claim 12, wherein the diamine represented by Chemical Formula 8 is represented by at least one of Chemical Formula 9 to Chemical Formula 11:

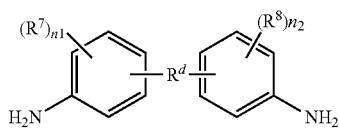

Chemical Formula 9 wherein, in Chemical Formula 9,
$R^d$ is selected from the following chemical formulae:

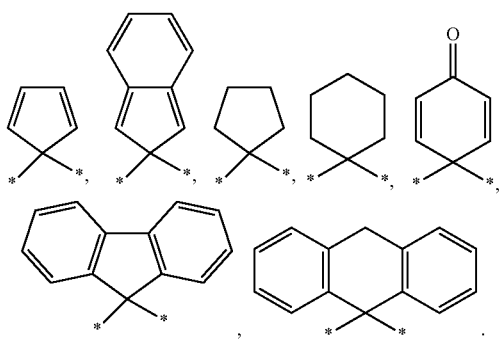

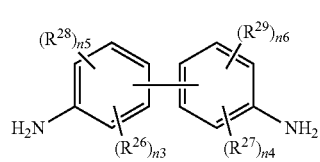

$R^7$ and $R^8$ are the same or different and are independently a halogen, a hydroxy group, an alkoxy group (—OR$^{200}$, wherein $R^{200}$ is a C1 to C10 aliphatic organic group), a silyl group (—SiR$^{201}$R$^{202}$R$^{203}$, wherein R$^{201}$, R$^{202}$, and R$^{203}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and
n1 and n2 are independently an integer ranging from 0 to 4;

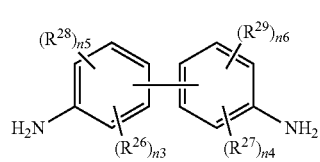

Chemical Formula 10 wherein, in Chemical Formula 10,
$R^{26}$ and $R^{27}$ are the same or different and are independently an electron withdrawing group selected from —CF$_3$, —CCl$_3$, —CBr$_3$, —Cl$_3$, —NO$_2$, —CN, —COCH$_3$, or —CO$_2$C$_2$H$_5$,
$R^{28}$ and $R^{29}$ are the same or different and are independently a halogen, a hydroxy group, an alkoxy group (—OR$^{204}$, wherein $R^{204}$ is a C1 to C10 aliphatic organic group), a silyl group (—SiR$^{205}$R$^{206}$R$^{207}$, wherein R$^{205}$, R$^{206}$, and R$^{207}$ are the same or different and are independently hydrogen or a C1 to C10 aliphatic organic group), a substituted or unsubstituted C1 to C10 aliphatic organic group, or a substituted or unsubstituted C6 to C20 aromatic organic group,
n3 is an integer ranging from 1 to 4, and n5 is an integer ranging from 0 to 3, provided that n3+n5 is an integer ranging from 1 to 4, and
n4 is an integer ranging from 1 to 4, and n6 is an integer ranging from 0 to 3, provided that n4+n6 is an integer ranging from 1 to 4;

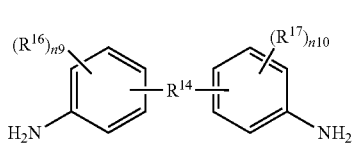

Chemical Formula 11 wherein, in Chemical Formula 11,
$R^{14}$ comprises O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, C(=O)NH, or a substituted or unsubstituted C6 to C18 aromatic organic group, wherein the substituted or unsubstituted C6 to C18 aromatic organic group is present as a single aromatic ring, a fused ring comprising two or more aromatic rings, or a ring system comprising two or more of the single aromatic ring and/or the fused ring that are linked by a single bond or a functional group of a fluorenylene group, O, S, C(=O), CH(OH), S(=O)$_2$, Si(CH$_3$)$_2$, (CH$_2$)$_p$ (wherein, 1≤p≤10), (CF$_2$)$_q$ (wherein, 1≤q≤10), C(CH$_3$)$_2$, C(CF$_3$)$_2$, or C(=O)NH, R$^{16}$ and R$^{17}$ are the same or different and are independently a halogen, a hydroxy group, an alkoxy group (—OR$^{212}$, wherein R$^{212}$ is a C1 to C10 aliphatic organic group), a silyl group (—SiR$^{213}$R$^{214}$R$^{215}$, wherein R$^{213}$, R$^{214}$, and R$^{215}$ are the same or different and are independently hydrogen or a C1 to C10 aliphatic organic group), a substituted or unsubstituted C1 to C10 aliphatic organic group, or a substituted or unsubstituted C6 to C20 aromatic organic group, and n9 and n10 are independently an integer ranging from 0 to 4.

14. The polymer of claim 13, wherein the diamine represented by Chemical Formula 8 comprises at least one of the diamine represented by Chemical Formula and the diamine represented by Chemical Formula 11, wherein the diamine represented by Chemical Formula 10 comprises 2,2'-bis(trifluoromethyl)benzidine (TFDB), and the diamine represented by Chemical Formula 11 comprises 4,4'-diaminodiphenyl sulfone (DADPS).

15. The polymer of claim 12, wherein an amount of the diamine represented by Chemical Formula 8 is less than or equal to about 50 mole percent based on a total amount of the monomer represented by Chemical Formula 1 and the diamine represented by Chemical Formula 8.

16. A compensation film comprising the polymer of claim 1.

17. An optical film comprising the compensation film of claim 16 and a polarizer.

18. A display device comprising the compensation film of claim 16.

19. A display device comprising the optical film of claim 17.

* * * * *